United States Patent [19]

Mekalanos et al.

[11] Patent Number: 5,512,452
[45] Date of Patent: Apr. 30, 1996

[54] SELECTION OF BACTERIAL GENES INDUCED IN HOST TISSUES

[75] Inventors: John J. Mekalanos, Cambridge; Andrew Camilli, Chestnut Hill, both of Mass.

[73] Assignee: President and Fellows of Harvard College, Cambridge, Mass.

[21] Appl. No.: 127,905

[22] Filed: Sep. 28, 1993

Related U.S. Application Data

[63] Continuation-in-part of Ser. No. 58,299, May 6, 1993, Pat. No. 5,434,065.

[51] Int. Cl.$^6$ .............................. C12Q 1/02; C12N 15/00
[52] U.S. Cl. .............................. 435/25; 435/172.3; 435/6; 935/76
[58] Field of Search ................................ 435/172.3, 6, 29, 435/317.1; 935/1, 6, 76, 111

[56] References Cited

PUBLICATIONS

Merryweather, A. et al. 1987. *Mol. Gen. Genet.* vol. 210 pp. 381–384.
Altenbuchner, J. 1993. *Gene* vol. 123 pp. 63–68.
Haas, R. et al. 1993. *Gene* vol. 130 pp. 23–31.
Berg, C. M. et al. 1992. *Gene* vol. 113 pp. 9–16.
Berg, C. M. et al. 1989. "Transposable Elements and the Genetic Engineering of Bacteria". In *Mobile DNA*, ed. D. E. Berg et al, American Society for Microbiology, Washington D.C., pp. 879–925.
"Environmental Signals Controlling Expression of Virulence Determinants in Bacteria," by J. Mekalanos, J. Bacteriology 174, 1 (1992).
"Mutants of *Salmonella typhimurium* that Cannot Survive With the Macrophage are Avirulent," by P. Fields, et al. Pro. Natl. Acad. Sci. USA 83, 5189–5193 (1986).
"A Single Genetic Locus Encoded by *Yersinia pseudotuberculosis* Permits Invasion of Cultured Animal Cells by *Escherichia coli* K–12," by R. Isberg, et al., *Nature*, 317, 262–264 (1985).
"Identification of Plant Induced Genes of the Bacterial Pathogen *Xanthomonas campestris* Pathovar campestris using a Promoter–Probe Plasmid," by A. E. Osbourn, et al. EMBO J., 6, 23–28 (1987).
"Two trans–acting Regulatory Genes (*vir* and *mod*) Control Antigenic Modulation in *Bordetella pertussis*," by S. Knapp, et al., J. Bacteriol 170, 5059–5066 (1988).
"Site–Specific Recombinase by the γδ Resolvase," by G. F. Hatfull, et al., Symp. Soc. Gen. Microbial., 43, 149–181 (1988).
"Transposon–Mediated Site–Specific Recombination: A Defined in Vitro System," R. Reed, *Cell* 25, 713–719 (1981).
"Selection of Bacterial Virulence Genes that are Specifically Induced in Host Tissues," M. Mahan, et al., *Science* 259, 686–688 (1993).
"New Technique Offers a Window on Bacteria's Secret Weapons," *Science* 259, 595 (1993).
"Bacterial Genetic Systems," J. M. Slauch, et al. *Methods Enzymol.*, 204, 212–248 (1991).

*Primary Examiner*—Mary E. Mosher
*Attorney, Agent, or Firm*—Steven C. Petersen; Chrisman, Bynum & Johnson

[57] ABSTRACT

A reporter system relating to in vivo expression technology was devised to aid in the identification and study of genes that display temporal or spatial patterns of expression during infection of host tissues. The method of this invention comprises integrating a site-specific DNA recombinase expression vector, and a reporter gene that is permanently removable by the recombinase, by way of homologous recombination into a microorganism's chromosome and inducing the expression of a synthetic operon which encodes transcripts, the expression of which are easily monitored in vitro and which result in a permanent genetic change, excision of the reporter gene, that is heritable and easily detectable subsequent to induction of the synthetic operon.

16 Claims, 11 Drawing Sheets

SELECTION OF BACTERIAL GENES INDUCED IN HOST TISSUES

CONTRACTUAL ORIGIN OF THE INVENTION

This study was supported by Cancer Research Fund of the Damon Runyon-Walter Winchell Foundation DRG-1201 (to A.C.) and National Institutes of Health Grant AI26289 (to J.J.M.).

CROSS-REFERENCE TO OTHER APPLICATIONS

This patent application is a continuation-in-part of U.S. patent application No. 08/058299, filed May 6, 1993, U.S. Pat. No. 5,434,065, and entitled In Vivo Selection of Microbial Virulence Genes.

BACKGROUND OF THE INVENTION

1. Field of the Invention:

The present invention relates to in vivo expression technology, and more particularly to a method of identifying and studying genes that display temporal or spatial patterns of expression during infection of host-tissues.

2. Description of the State of the Art:

An infection of the human body by a pathogen, or disease-producing microorganism, results in disease when the potential of the microorganism to disrupt normal bodily functions is fully expressed. Some disease-producing microorganisms possess properties, referred to as virulence factors, that enhance their pathogenicity and allow them to invade host or human tissues and disrupt normal bodily functions. The virulence of pathogens, that is, their ability to induce human disease, depends in large part on two properties of the pathogen, invasiveness and toxigenicity. Invasiveness refers to the ability of the pathogen to invade host or human tissues, attach to cells, and multiply within the cell or tissues of the human body. Toxigenicity refers to the ability of a pathogen to produce biochemicals, known as toxins, that disrupt the normal functions of cells or are generally destructive to cells and tissues.

Scientists can develop better therapeutic and diagnostic approaches against pathogenic microbes if they understand better the molecular mechanisms of the specific pathogenic microbes or microorganisms that allow them to circumvent the host's, e.g., human body, immune system and initiate the physiological changes inherent in the disease process. To do so, scientists must identify those virulence factors, or microbial gene products, that are specifically required for each stage of the infection process. Environmental conditions within the host are responsible for regulating the expression of most known virulence factors (J. Mekalanos, 1992, *J. Bacteriol.* 174:1). Consequently, scientists attempt to mimic, in vitro, the environmental conditions within the host in an attempt to identify and study those genes that encode and are responsible for producing virulence factors. As a result, the ability to identify and study the expression of many virulence factors has been dependent on, and limited by, the ability of researchers to mimic host environmental factors in the laboratory.

There have been some methods developed for identifying and studying the expression of virulence genes of microorganisms involved in pathogenesis. For example, a method referred to as insertional mutagenesis has long been recognized as a technique to inactivate and identify genes. Insertional mutagenesis relies on the ability of short stretches of DNA, known as insertion sequences, to move from one location to another on a chromosome by way of nonreciprocal recombination. Insertion sequences are not homologous with the regions of the plasmid or the chromosome into which it is inserted. Therefore, independent mutational events may be generated by randomly inserting an insertion sequence into a gene, thereby, disrupting the expression of that gene. As each mutated gene represents a different case, the selection procedure utilized in successfully recovering insertional mutants is critical. In vitro assays are designed to screen for insertional activation events, i.e., the turning "on" of a previously silent gene, or insertional inactivation events, i.e., the turning "off" of a previously expressed gene. For an example of the insertional mutagenesis method. Fields, et al., 1986, *Proc. Natl. Acad. Sci.* USA 83:5189–5193.

The second basic technique utilized in the identification of genes is referred to as a cloning screen. Essentially, a piece of DNA or gene from the organism of interest is spliced into either a plasmid or a lambda phage, referred to as the vehicle or vector, and the resulting chimefie molecule is used to transform or infect, respectively, a host cell. A determination is then made as to whether the piece of DNA or gene of interest is capable of conferring a specific phenotype to the host cell which it would not otherwise possess, but for the gene of interest. For example, in a technical paper (R. Isberg, et al., "A Single Genetic Locus Encoded by *Yersinia pseudotuberculosis* Permits Invasion of Cultured Animal Cells by *Escherichia coli* K-12," *Nature*, 1985, 317:262–264) a cloning screen is disclosed in which a cosmid clone bank is prepared from *Y. pseudotuberculosis* genomic DNA and introduced into a bacterial *E. coli* K-12 strain. The *E. coli* K-12 strain containing random sequences of DNA representing the entire genetic information for *Y. pseudotuberculosis* was pooled, grown in broth, i.e., a complete medium, and used to infect a monolayer of cultured HEp-2 cells, i.e., animal cells. The cultured animal cells were then cultured and tested to determine whether introducing DNA from *Y. pseudotuberculosis* to *E. coli* confers an invasive phenotype typical of *Y. pseudotuberculosis* to *E. coli*.

A third method discussed by A. Osbourn, et al., entitled "Identification of plant induced genes of the bacterial pathogen *Xanthornonas campestris* pathovar *campestris* using a promoterprobe plasmid" (EMBO J., 1987, 6:23–28) discloses a promoter probe plasmid for use in identifying promoters that are induced in vivo. Random chromosomal DNA fragments are cloned into a site in front of a promoterless chloramphenicol acetyltransferase gene contained on a plasmid. Transconjugates were then produced by transferring the resulting library into Xanthornonas. Individual transconjugates are then introduced into chloramphenicol-treated seedlings to determine whether the transconjugate displays resistance to chloramphenicol in the plant and then on an agar plate.

The final method utilized in the identification of genes is referred to as a regulatory screen. S. Knapp, et al., in his technical publication, entitled "Two Trans-Acting Regulatory Genes (vir and rood) Control Antigenie Modulation in *Bordetella pertussis*," (*J. Bacteriol*, 1988, 170:5059–5066) discloses a method for identifying potential virulence genes based on their coordinate expression with other known virulence genes under defined laboratory conditions.

Transcriptional fusions to heterologous reporter genes such as β-galactosidase and chloramphenicol-acetyl transferase have been extensively used to study gene expression in both prokaryotic and eukaryotic organisms (Slauch, J. M. & Silhavy, T. J., 1991, *Methods Enzymol.* 204:212–248).

3

Although they provide an elegant method in most instances, these reporter fusion systems are technically limited to assaying expression within large populations of the test organism and are at times dictated by the reporter half-life. These limitations are particularly troublesome when complex systems are being probed, i.e., studying gene expression by pathogenic microbes during infection of a host organism.

The above technical papers by Fields, et al., R. Isberg, et al, and S. Knapp, et al., each disclose methods for identifying microorganismal genes; however, the selection procedures or in vitro assays utilized in each method depends upon the ability of the in vitro assay to mimic the environmental conditions within the host, i.e., the in vivo environmental conditions. A disadvantage of these approaches is that each requires some understanding of the environmental conditions necessary to obtain virulence gene expression. Furthermore, the ability to study the spatial and temporal expression of these genes is also limited. Consequently, scientists have resorted to mixing host cells with the pathogen of interest in vitro to approximate the host's environmental conditions. Short of an exact duplication of the host's environmental conditions, critical regulatory factors necessary for the expression of many virulence factors may be missing, thus making the identification and study of those genes responsible for encoding virulence factors impossible.

While the technical paper by A. Osbourn, et al., discloses a method to screen for promoters that are induced in vivo, a disadvantage is that no feasible method exists to select genes of a particular class, that is, individual transconjugates must be screened one by one in individual seedlings to determine whether a promoter is inducible. A further disadvantage results from a phenomena referred to as a position effect. A. Osbourn, et al., utilizes an autonomous plasmid and therefore the regulation of the promoter may vary considerably from the regulation of the promoter as it is found in its natural environment on the Xanthomonas genome. Other complications that arise from the use of plasmids are copy number, stability and supercoiling effects.

There is still a need, therefore, for a method or technique for identifying and studying genes encoding virulence factors in their normal environment whose expression is regulated, or turned "on", by undetermined factors within the host.

SUMMARY OF THE INVENTION

Accordingly, it is an object of this invention to provide a method for identifying and studying microbial genes that are specifically induced within the host tissues.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein, the method of this invention comprises integrating a site-specific DNA recombinase expression vector, and a reporter gene that is permanently removable by the recombinase, by way of homologous recombination into a microorganism's chromosome and inducing the expression of a synthetic operon which encodes transcripts, the expression of which are easily monitored in vitro and which result in a permanent genetic change, excision of the reporter gene, that is heritable and easily detectable subsequent to induction of the synthetic operon.

BRIEF DESCRIPTION OF THE DRAWINGS In
The Drawings:

The accompanying drawings, which are incorporated herein and form a part of the specification illustrate preferred embodiments of the present invention, and together with the description, serve to explain the principles of the invention. Furthermore, the accompanying drawings due to size limitations are not drawn to scale.

Figure 12:
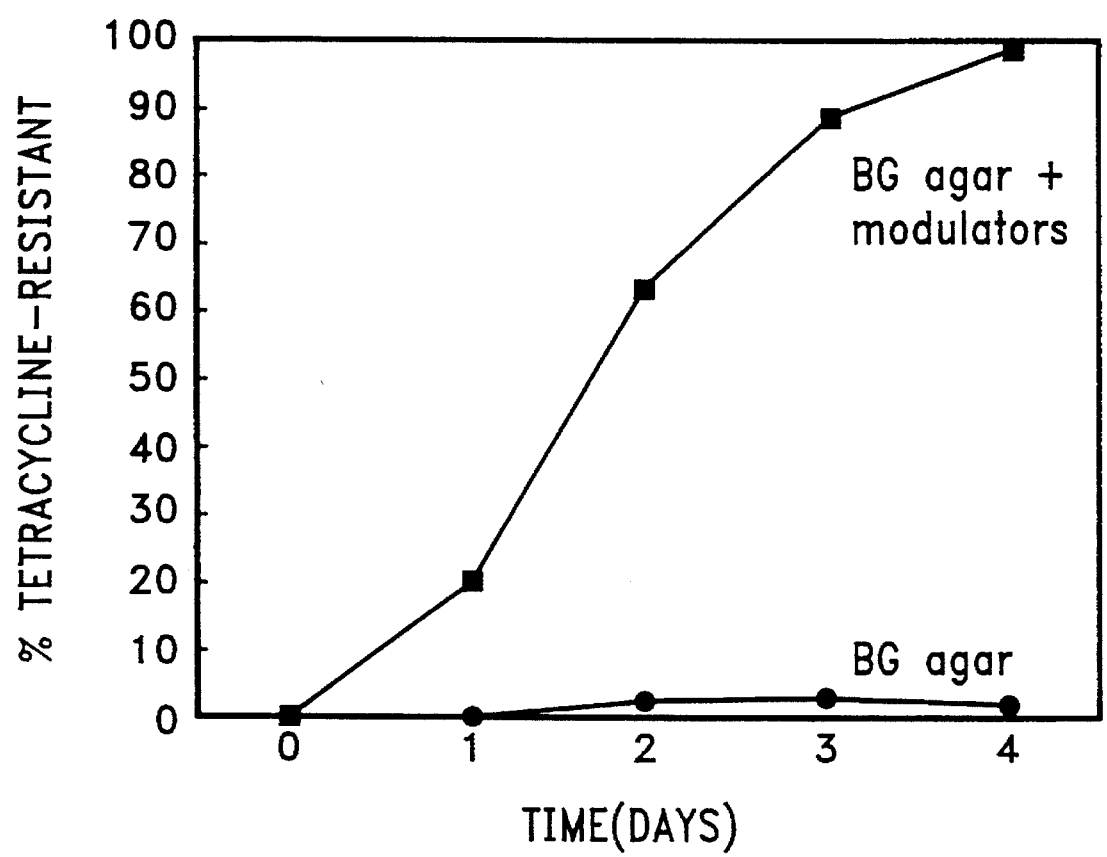

FIG. 12 is a comparison of the Bordetella pertussis vrg6 gene expression in inducing and non-inducing environments in vitro using the products of genetic recombination (loss of tetracycline-resistance) as a reporter. The vertical axis depicts the percentage of the bacteria which were tetracycline-sensitive versus time shown on the horizontal axis. The closed circles denote the tetracycline-sensitive bacteria grown on Bordet-Gengou blood agar. The closed boxes denote the tetracycline-sensitive bacteria grown on Bordet-Gengou blood agar supplemented with the modulators $MgSO_4$ and nicotinate.

DETAILED DESCRIPTION OF THE
PREFERRED EMBODIMENT

Figure 1:
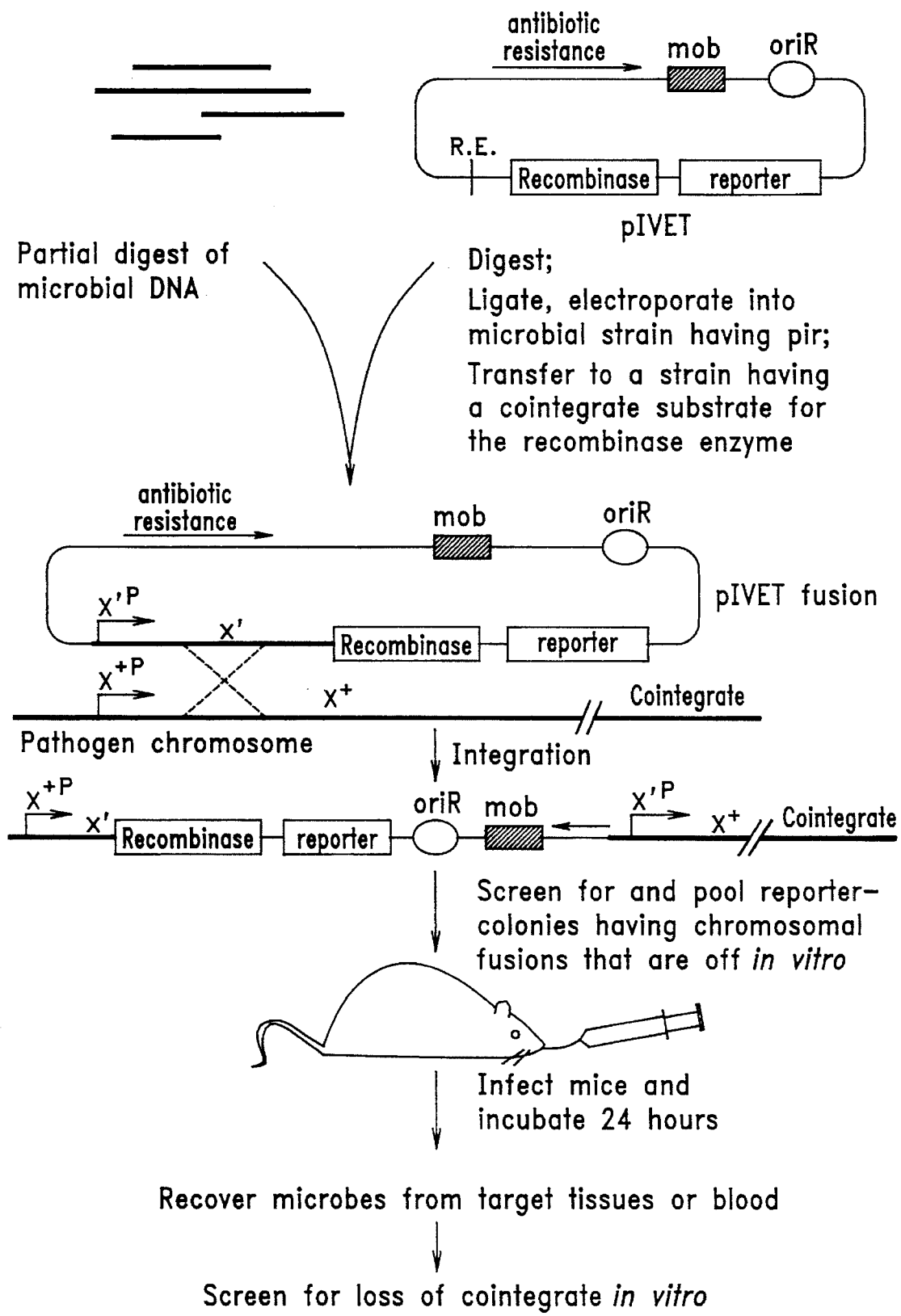
FIG. 1 is a flow sheet representing the method of screening for genes that are induced in the host.
Figure 2:
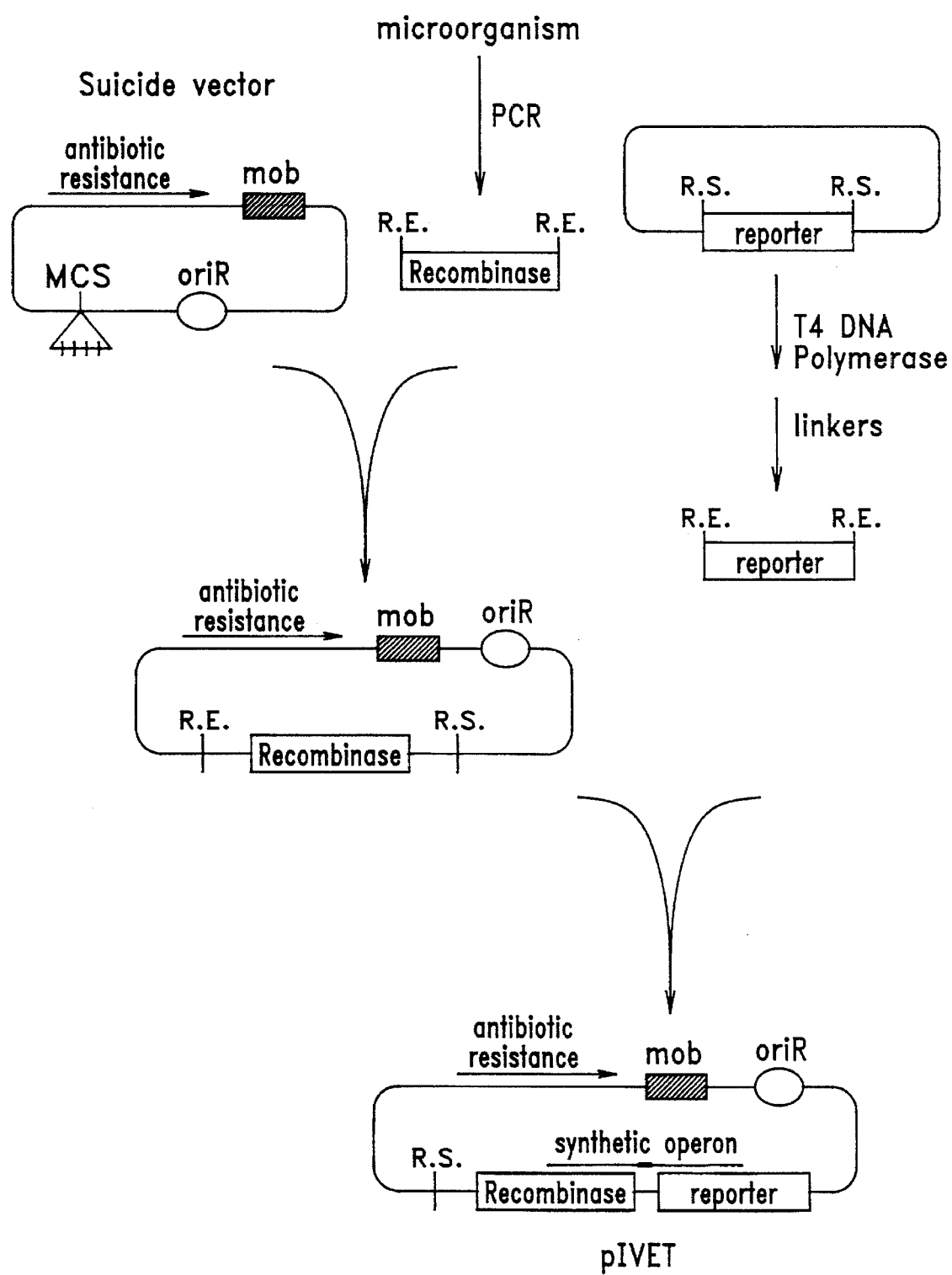
FIG. 2 is a diagrammatic representation of the construction of the pIVET vector.

The genetic method or reporter system, according to this invention, as shown in FIG. 1, does not rely on the reproduction of the host's environmental signals in the laboratory, but rather depends directly upon the induction or activation of microbial genes within the host itself. Plasmid or vector pIVET, constructed as shown in FIG. 2, provides several significant functions for purposes of this invention. First, vector pIVET provides a method for introducing and integrating a single copy of foreign genetic material or DNA into the recipient organism's genome, thereby avoiding any complications such as copy number, stability or supercoiling effects that may arise from the use of plasmids that replicate autonomously within the cell. Second, the integration event does not disrupt any chromosomal genes of the recipient microorganism. If a gene of interest encodes a product required for the infection process, i.e., a virulence factor, then any integration event which disrupts the gene would not be recoverable. Third, the transcriptional activity of the integrated foreign DNA can be monitored both in vitro and in vivo.

Plasmid pIVET comprises a suicide vector for receiving and introducing foreign genetic material into a recipient cell, a synthetic operon for expressing gene products which are easily monitored both in vitro and in vivo, and a restriction or cloning site (shown as R.S. in FIG. 2) for cloning a random homologous fragment of chromosomal DNA. The pIVET vector having a cloned fragment of DNA is referred to as a pIVET fusion.

Suicide vectors are essentially shuttle vectors that provide a means for introducing foreign genetic material into a recipient cell. However, unlike a typical shuttle vector, suicide vectors have replicons that are not independently maintainable within the recipient cells, i.e., as the cells propagate, the suicide vector, being incapable of autonomous replication, will be lost in subsequent cells. Consequently, integration of the pIVET fusion into the recipient cell's genome is required for the continued survival of the pIVET fusion within the recipient cell. One of the genes present on the suicide vector encodes for antibiotic resistance, such as the β-lactamase or bla gene, which confers resistance to the antibiotic ampicillin. Therefore, a simple and convenient method of monitoring whether integration of the pIVET fusion, into the recipient's genome, has occurred is to expose the recipient cells to an antibiotic for which they are typically sensitive and to select those cells which are resistant. Cells that display resistance to the antibiotic are those which have the pIVET fusion integrated into and replicated with the recipient cell's genome. Those cells in which the pIVET fusion was not integrated into the genome eventually lose the pIVET fusion and remain sensitive to the antibiotic.

Essentially, the reporter system of the present invention originates with a microorganism or reporter strain that is carrying an artificial transposon-encoded recombination system consisting of an antibiotic resistance gene flanked by directly repeated recombination sequences. Transposons or translocatable genetic elements are well known and extensively studied. An example of a transposon recombination system is that of the γδ transposon or Tn,γδ. The process of integrating Tnγδ into a chromosomal region results in the formation of a cointegrate. The cointegrate contains two identically oriented copies of γδ. Resolution or excision of the cointegrate requires action of the tnpR gene product, resolvase, which recognizes a specific DNA sequence of 120-bp called res resulting in the non-replicating DNA mini-circle containing the excised tetracycline-resistance gene. Resolution only takes place intra-molecularly and thus, cointegrate resolution is an irreversible reaction.

The reporter system, according to the present invention is accomplished through the construction of microorganisms or reporter strains that have a cointegrate, i.e., an antibiotic resistance gene flanked by directly repeated recombination sequences. In the alternative the cointegrate may comprise a visual reporter gene flanked by directly repeated sequences. Presence of the antibiotic gene on the cointegrate confers an antibiotic resistance phenotype to the microorganism to that specific antibiotic. Resolution of the cointegrate is further accomplished through the construction, introduction, and expression of a recombinase gene isolated in the synthetic operon, which in turn leaves the microorganism once again sensitive to the specific antibiotic which the presence of the cointegrate confers resistance.

As shown in FIG. 2, the synthetic operon is comprised of two promoterless genes that have been isolated and fused together directionally oriented downstream of the pIVET cloning or restriction site. Orientation refers to the directionality of the structural gene. That portion of a structural gene which ultimately codes for the amino terminus of the protein is termed the 5'-end of the structural gene, while that end which codes for the amino acid near the carboxyl end of the protein is termed the 3'-end of the structural gene. Correct orientation of the structural gene is with the 5'-end thereof proximal to the promoter. A promoter contains specific DNA base-pair sequences which lie at the 5'-end of a gene and are responsible for binding an enzyme, RNA polymerase, which initiates transcription of a gene. These base-pair sequences are not gene specific; therefore, a promoter region operatively linked to any gene or set of genes will control the expression of that gene or that set of genes, respectively, dependent on the proper regulatory factors or enzyme modifications being present to allow RNA polymerase to recognize the specific transcription sites. The region of DNA lying under promoter control is said to lie "downstream" or alternatively "behind" or "3' to" the promoter. Therefore, to be controlled by the promoter the correct position of the gene must be downstream from the promoter. However, the synthetic operon as constructed lacks the specific base pair sequences necessary for the initiation of transcription. Therefore, the products encoded for by the synthetic operon are incapable of being expressed unless a promoter sequence exists in the region of the recipient's chromosome that is homologous to the fragment of DNA which is inserted into the cloning site of the pIVET vector situated 5' to the synthetic operon.

The first gene of the synthetic operon, i.e., the gene lying immediately downstream from the cloning site, encodes an enzyme or site specific DNA recombinase which mediates resolution of the cointegrate. Resolution of the cointegrate results in an antibiotic sensitive phenotype for the reporter strain, specific to the antibiotic resistance gene found on the cointegrate.

The second gene of the synthetic operon is a reporter gene that lies immediately downstream from the first gene and encodes a reporter enzyme. Expression of the reporter gene can be easily detected by calorimetric assays which are well known and understood in the art. Furthermore, the fusion strain does not contain a gene homologous to the reporter gene. Consequently, the only site in the pIVET vector capable of homologous recombination with the recipient's chromosome is that fragment of DNA which is cloned into the restriction site 5'to the synthetic operon.

Referring now to FIG. 1, total genomic DNA is isolated from the parental strains of the reporter strain and then partially enzymatically digested, resulting in a pool of random chromosomal fragments. The pIVET vectors, which have previously been cleaved at the restriction or cloning site, are then mixed into this pool of random chromosomal fragments. The chromosomal fragments are ligated into the pIVET vectors to produce a library of pIVET fusions, i.e., each pIVET fusion contains a random chromosomal fragment so that the pool of pIVET fusions is representative of the entire fusion strains genome. The pIVET fusions are then electroporated into a microorganism that supplies the replication protein, Pi, which is required for replication by the suicide vector, as will be discussed in further detail below. The pIVET fusions are then introduced or injected into the reporter strain, by well known methods, for example, transduction, transformation, electroporation, tri-parental mating technique or direct transfer of a self-mobilized vector in a hi-parental mating, thereby producing exconjugates.

After the pIVET fusion is introduced into the reporter strain, a couple of possible events may occur. For example, since the plasmid is unable to replicate, it may be diluted out or degraded in progeny bacterial cells, or there could be integration of the pIVET fusion into the reporter strain's genome by homologous recombination. The former event occurs most often because integration of a plasmid by homologous recombination is an inefficient process. The latter event of integration through a processes referred to as homologous recombination is an essential step to the method of the present invention, and this event can be selected by the use of antibiotics as described previously. As discussed above the only DNA sequences of the pIVET fusion that share sufficient homology with the chromosome of the recipient strain to allow the recombination event are those random chromosomal fragments which were inserted 5' to the synthetic operon. Consequently, only these random fragments share sufficient homology with the recipient's genome, and it is through these homologous sequences of DNA that the integration event of the pIVET fusion and the recipient cell's genome takes place, thus resulting in a fusion strain.

Figure 3:
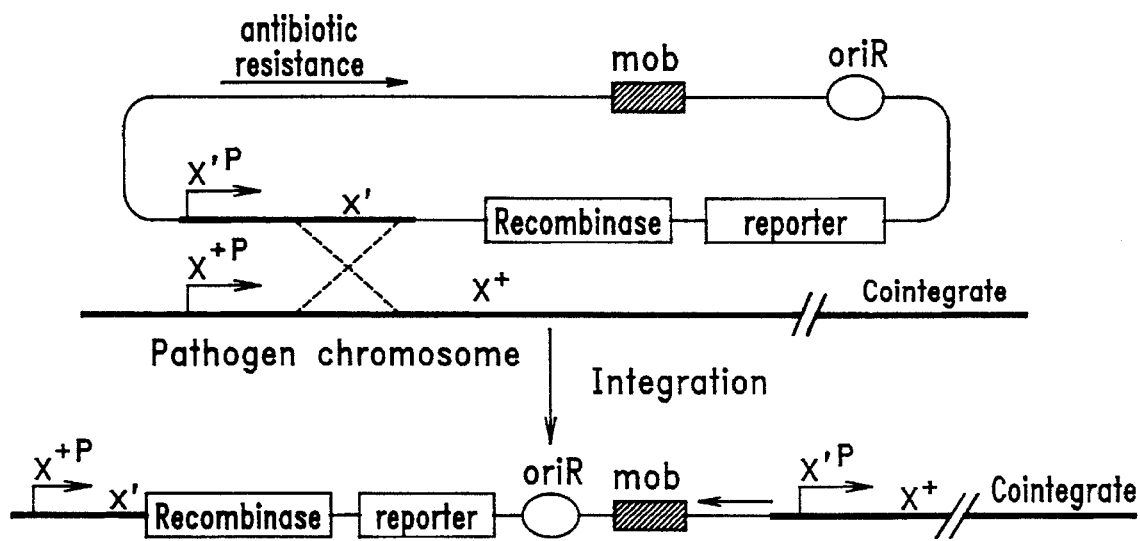
FIG. 3 is a diagrammatic representation of the homologous recombination event which occurs between the pIVET fusion and the pathogen chromosome.
Figure 3A:
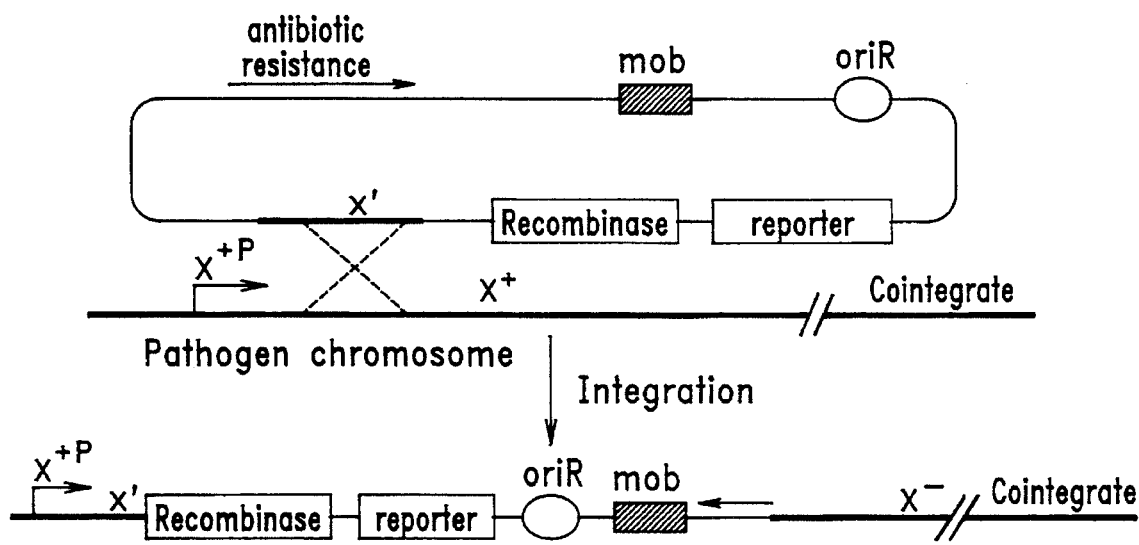
FIG. 3a is a diagrammatic representation of the manner in which the expression of a wild type gene on the pathogen chromosome may be disrupted as a result of the homologous recombination event with the pIVET fusion which lacks a cloned promoter region.

The desired integration event is illustrated in FIG. 3. The cloned chromosomal fragment X' containing a promoter sequence $X'^p$ is homologous to and recombines with its respective or wild type sequence $X^+$ located in the reporter strain's chromosome. The promoter of the wild type gene designated $X^{+p}$ is now operatively linked to and controls the expression of the synthetic operon, whereas the wild type gene, $X^+$, of the reporter strain is now linked to and under the control of the $X'^p$ promoter. The importance of this event is that the integration event does not disrupt any chromosomal genes that may be necessary for the infection process. The manner in which an integration event could lead to the disruption of a chromosomal gene is illustrated in FIG. 3a. The chromosomal fragment X' inserted into the pIVET vector may not have a promoter sequence, or the promoter sequence may be in the wrong orientation with respect to the gene (not shown) which it is to control. In either event, homologous recombination will occur between the cloned chromosomal fragment, X', and the reporter strain's chromosome, $X^+$. However the promoter of the wild type gene, $X^{+p}$, will initiate transcription of the synthetic operon, while the wild type gene will not be expressed, since it will now lack a promoter. If the wild type gene, X, that is disrupted through this integration event is essential to the infection process it will not be recoverable as those microorganisms will not be infectious and will survive within the host.

The exconjugates, i.e., the strain resulting from the mating of the microorganisms carrying the pIVET fusions with the reporter strains, from each mating are plated out and individual colonies are selected by calorimetric assays as well as antibiotic selection. Those colonies having no detectable color shift and a resistant phenotype, to the antibiotic on the cointegrate, have inactive synthetic operons and are of further interest. Therefore, these colonies are grown and pooled together.

As shown in FIG. 1, the pool of exconjugates having inactive synthetic operons are used to infect a host. After a period of infection, the host is sacrificed and the organs, tissues, or blood which are the targets of infection for the pathogenic microorganism used to infect the host are removed and homogenized. The microorganisms are harvested and then cultured and plated out on a medium that does not contain the antibiotic that the cointegrate confers resistance. The colonies are then replica-plated on a medium, which does contain the antibiotic that the cointegrate confers resistance. Colonies that do not grow on the replica-plate indicate that the expression of the site specific DNA recombinase gene of the synthetic operon was induced or turned "on" in vivo resulting in the irreversible resolution of the cointegrate. Thus, rendering the microorganism sensitive to that particular antibiotic.

Thus, those antibiotic sensitive microorganisms recovered from the host-passaged pools that display an antibiotic sensitive phenotype each contain chromosomal gene fusions to the synthetic operon that were transcriptionally active at some time and place during the host infection.

Figure 10:
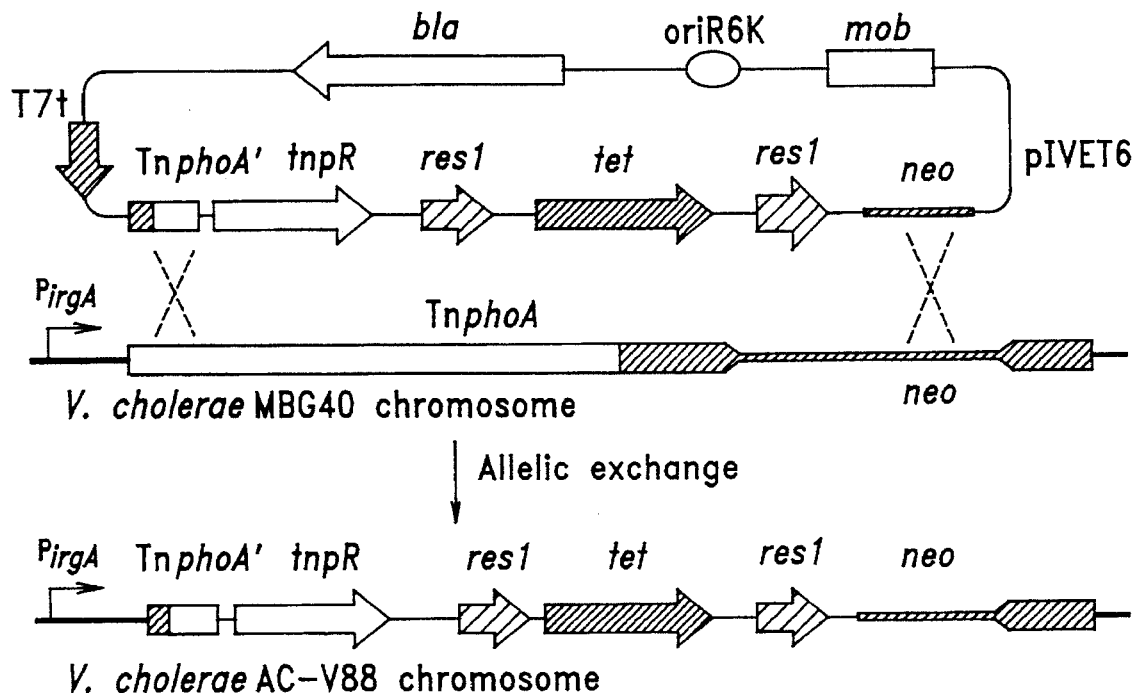
FIG. 10 is a diagrammatic representation of allelic exchange of pIVET6 with a chromosomal copy of TnphoA inserted into V. cholerae irgA.

In another embodiment the reporter system of the present invention (not shown) may be accomplished through the construction and expression of a promoterless gene located on a suicide vector having an artificial cointegrate. The promoterless gene is located downstream from a restriction site in which promoter sequences may be inserted. Induction of the promoter sequence will result in the expression of an enzyme required for the resolution of the cointegrate. The cointegrate as described previously in the first embodiment comprises an antibiotic resistance gene flanked by directly repeated recombination sequences. The pIVET vector having the cointegrate is then inserted into a microorganism that is sensitive to the antibiotic for which the cointegrate confers resistance. Exconjugates are produced as described above and used to infect a host organism. Antibiotic sensitive exconjugates that result following host infection occur due to the resolution of the cointegrate. It is through the appearance of these antibiotic sensitive exconjugates that the temporal or spatial patterns of expression of the promoter sequence during the infection process are monitored. In a third embodiment, a suicide vector, shown in FIG. 10, is designed to facilitate the integration of the reporter system of the present invention into the genome of microorganisms carrying inserts of TnphoA. The first gene segment of the synthetic vector encodes the 5' portion of TnphoA and is only present for the purposes of presenting a site in which allelic exchange may occur between the chromosome of the exconjugate to be produced and the pIVET vector. Fused to the 3' end of the TnphoA 5' portion is a promoterless gene which encodes an enzyme, the expression of which results in the resolution of the artificial cointegrate located directly down-stream from the promoterless gene. Finally, located 3' to the cointegrate, a downstream portion of TnphoA exists and is present as a site for allelic exchange. As is shown in FIG. 10, a double crossover event leads to the formation of the exconjugate. The recombination event that occurs between the upstream portion of TnphoA and the downstream portion of TnphoA results in the integration of the cointegrate into the genome of the microorganism and generation of a transcriptional fusion of the upstream chromosomal promoter with the formerly promoterless gene. This reporter system may be used to assay temporal or spatial patterns of expression in microorganisms carrying fusions between target genes and phoA.

In a fourth embodiment, (not shown), the reporter system of the present invention may be accomplished through the construction and expression of a promoterless gene located on a plasmid having an artificial cointegrate. The promoterless gene is located downstream from a restriction site in which promoter sequences may be inserted. Induction of the promoter sequence will result in the expression of an enzyme required for the resolution of the cointegrate. The cointegrate as described previously in the first embodiment comprises an antibiotic gene flanked by directly repeated sequences. The plasmid having the cointegrate is then inserted and maintained autonomously within a microorganism that is sensitive to the antibiotic for which the cointegrate confers resistance. The above-described embodiment will be beneficial in bacterial species, such as mycobacterium, that do not have good homologous recombination.

Modifications of the present invention where the antibiotic-resistance reporter gene of the cointegrate is replaced with a visible reporter or other selectable marker that functions in eukaryofic cells might be applied to studying gene expression in viruses and eukaryofic cells. All reporter strains to date contain a cointegrate having res sites derived from Tnγδ. The availability of various res mutant sequences exhibiting a wide range of resolution potential should facilitate these and other future studies by allowing one to alter the resolution levels mediated by a particular tnpR-gene fusion. Of course, regardless of whichever reporter system is ultimately used, the method of this invention will require a method of monitoring transcriptional activity in order to determine whether the reporter system was induced or activated, thereby indicating which microorganisms can be selected for purposes of this invention. The reporter system of the present invention was designed to facilitate the study of expression as well as the identification of genes which encode for virulence factors, not only in bacteria, but also in other pathogenic microorganisms, including viruses, bacteria, parasites, fungi and protozoa thereby contributing to vaccine and antimicrobial drug development. For example, in vivo induced genes may encode new antigens, and mutations in in vivo induced genes may provide an additional means of constructing live attenuated vaccines. Multivalent vaccines in which a single live vaccine is engineered to make several antigens, immunizing against several diseases at once could also be designed with the identification of new virulence genes.

Example 1 below demonstrates the utility of the reporter system of the present invention to screen for virulence genes which are expressed in vivo during infection of a host organism. Example 2 demonstrates that the reporter system of the present invention serves as a useful tool for the study of temporal or spatial gene expression. The efficacy of the reporter system of the present invention was studied by converting two well characterized bacterial pathogen genes into transcriptional fusions to tnpR.

EXAMPLE 1

Construction of the pAC20 and pAC21 Vector

All enzymes were purchased from New England Biolabs, Inc., 32 Tozer Road, Beverly, MA 01915-5599, unless specified otherwise and, were used according to the manufacturer's instructions. Standard molecular biology protocols were used according to Sambrook, J. et al, Molecular Cloning, A Laboratory Manual, 2nd ed., 1989, Cold Spring Harbor Laboratory Press.

The tnpR gene of Tnγδ encodes the site-specific recombinase enzyme, resolvase. Resolvase specifically binds to and catalyzes strand exchange between two directly repeated 120-bp DNA sequences (res sequences) that are intramolecular within a double-stranded supercoiled DNA molecule (the substrate). The reaction is irreversible and results in the excision of the intervening DNA between the two res sequences giving two separate DNA molecules as the reaction products (Benjamin, H. W., et al., 1985, *Cell* 40:147–158).

Figure 4:
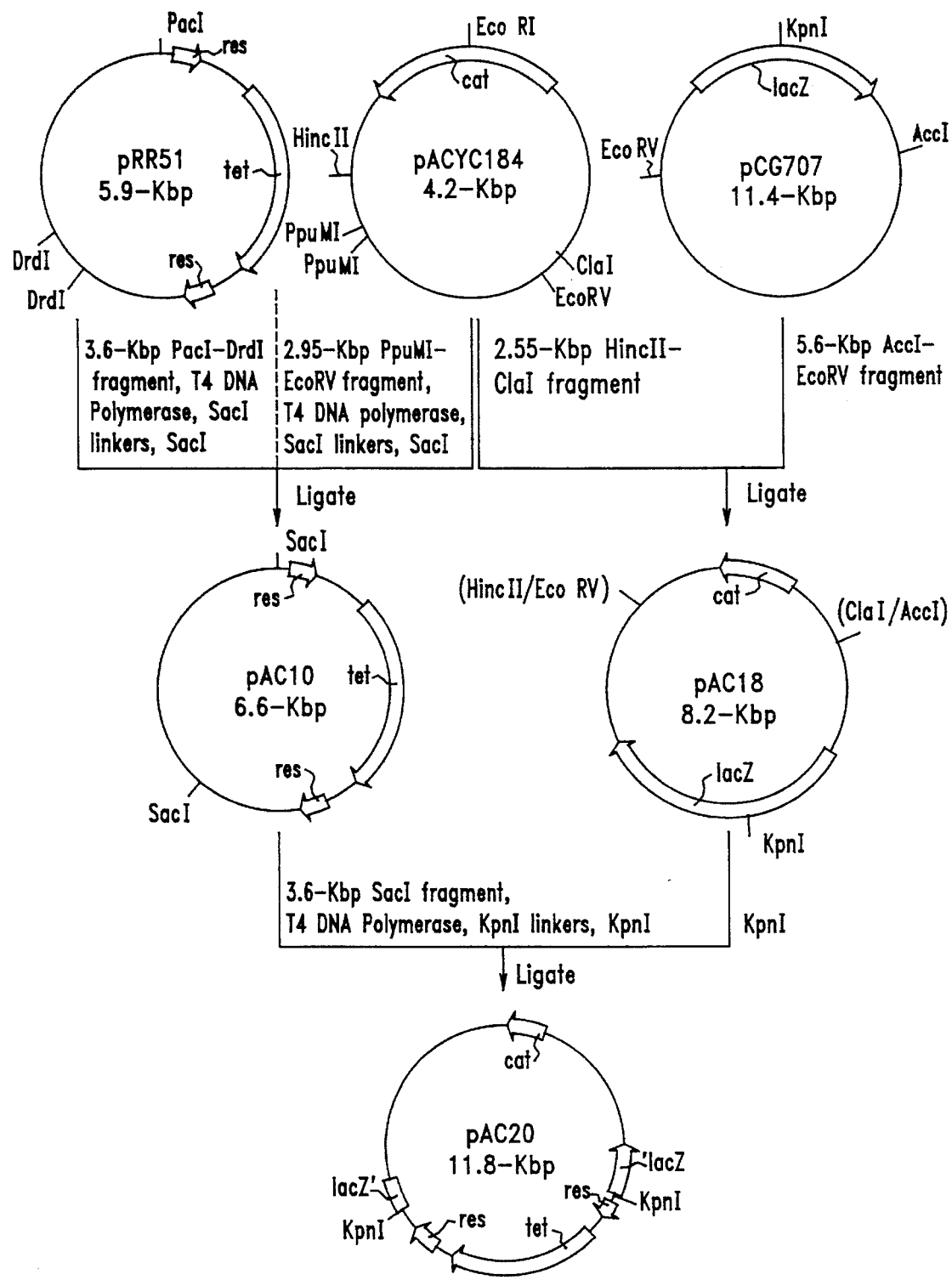
FIG. 4 is a diagrammatic representation of the construction of the pAC20 vector.

The reporter system of the present invention involves generating libraries of great numbers of different gene fusions to tnpR, it was therefore desirous to avoid possible influences that local chromosomal environments may have on the resolution potential of the res1 tet res1 or res tet res substrates. To accomplish this, two parental strains, for introducing tnpR gene fusions into, were generated which already contain either the res1 tet res1 or res tet res substrate integrated into one chromosomal site, within the *V. cholerae* lacZ gene. For the purpose of nomenclature simplification, we have designated the mutant res DNA sequence containing a T to C transition mutation at the cross-over site (Stark, W. M., et al., 1991, EMBO 10:3541–3548) as res1 (Camilli, A., et al., submitted). To generate these parental strains two allelic exchange vectors, pAC20, shown in FIG. 4 and pAC21 shown in FIG. 5, were constructed and used to replace the lacZ allele on the chromosome of *V. cholerae* with either lacZ::res1 tet res1 or lacZ::res tet res. pAC20 and pAC21 were constructed as described in further detail below.

A 5.6-kbp Eco RV and Acc I restriction fragment from pCG707 (Gardel, C. L. & J. J. M., unpublished) carrying the *V. cholerae* lacZ gene and surrounding sequences was inserted into the 2.55-kbp Hinc II and Cla I fragment of pACYC184 (Change, A. C. Y. & Cohen, S. N., 1978, *J. Bacteriol.* 134:1141–1156), to generate pAC18. This resulted in replacement of the pACYC184 tet gene with the *V. cholerae* lacZ gene and surrounding sequences. A 3.6-kbp Pac I and Drd I restriction fragment of pRR51 carrying res tet res was inserted into the 2.95-kbp Eco RV and Ppu MI fragment of pACYC184 after filling in the DNA ends with T4 DNA polymerase, adding Sac I linkers and digesting with Sac I to generate pAC10. Then the 3.6-kbp Sac I fragment of pAC10 containing res tet res was inserted into the unique Kpn I site of pAC18 which lies within the *V. cholerae* lacZ coding sequence on pAC18, to generate pAC20 shown in FIG. 4. The orientation of the insert was such that the tet gene is transcribed opposite to that of the lacZ gene in which it is inserted. pAC20 was electroporated into *E. coli* MC1061 (Wertman, K. F., et al., 1986, *Gene* 49:253–262) and the resulting strain was maintained by growth on LB agar supplemented with Sin, 100 μg/ml; Tc, 3 μg/ml; and Cm, 10 μg/ml.

Figure 5:
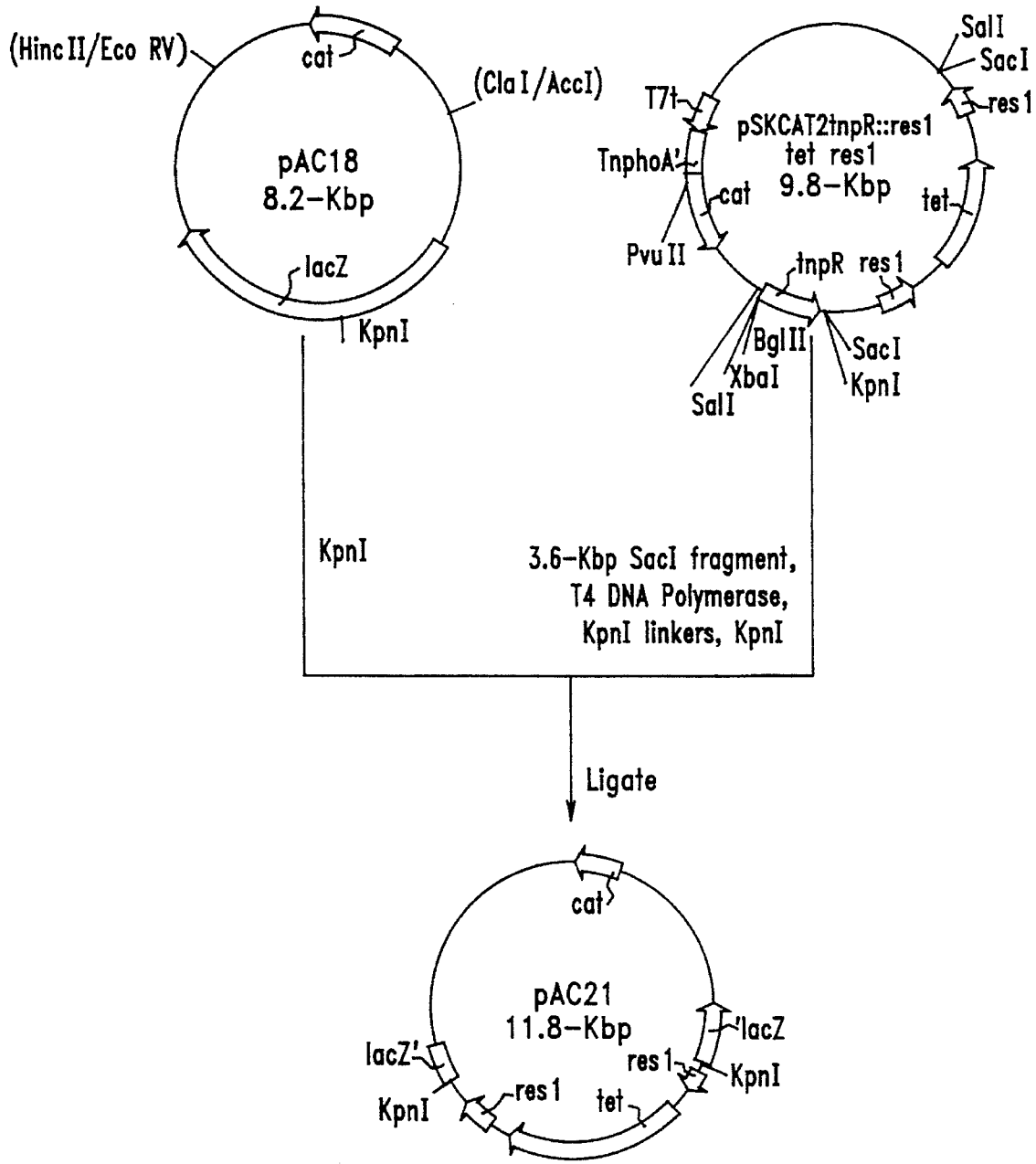
FIG. 5 is a diagrammatic representation of the construction of the pAC21 vector.
Figure 6:
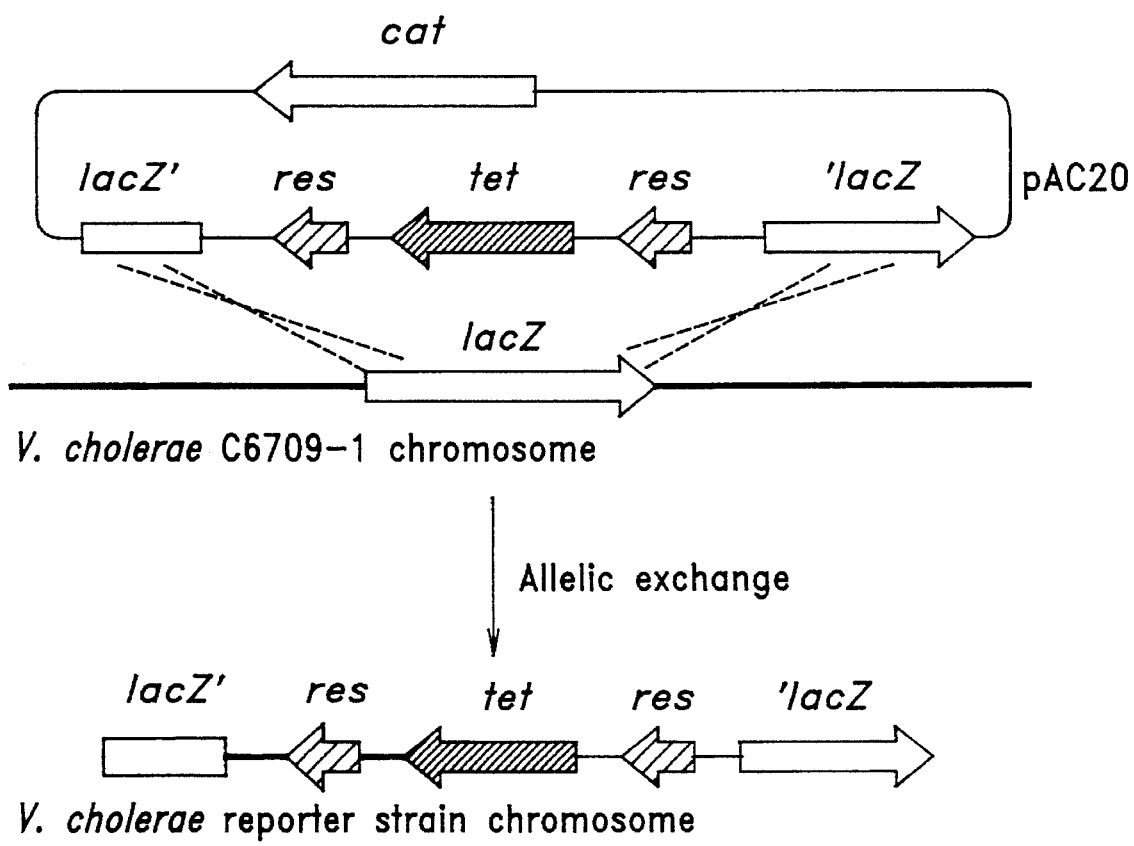
FIG. 6 is a diagrammatic representation of the allelic exchange event which occurs between the segment of pAC20 bounded by the V. chololerae lacZ sequences and the V. cholerae chromosomal lacZ allele.
Figure 7:
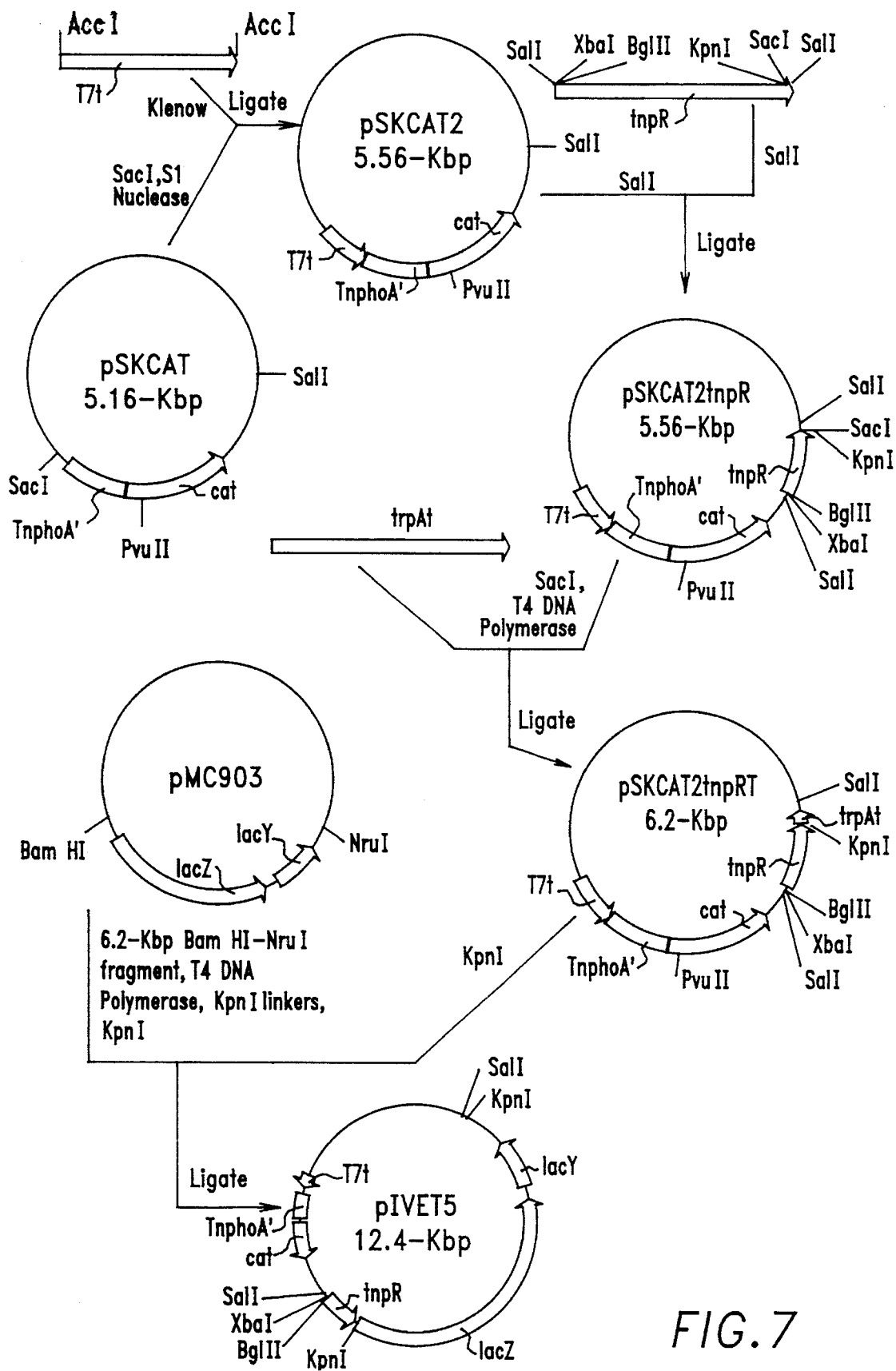
FIG. 7 is a diagrammatic representation of the construction of the pIVET5 vector.

To generate pAC21, a 3.6-kbp Sac I fragment containing res1 tet res1 was isolated from pSKCAT2tnpR::res1 tet res1, as shown in FIG. 5, and described in Example 2 below, the DNA ends were filled in with T4 DNA polymerase, Kpn I linkers were added, and the resulting fragment was digested with Kpn I and inserted into the unique Kpn I site of pAC18 which lies within the *V. cholerae* lacZ coding sequence on pAC18, to generate pAC21. pAC21 was electroporated into *E. coli* MC1061 and the resulting strain was maintained by growth on LB agar supplemented with Sm, 100 μg/ml; Tc, 3 μg/ml; and Cm, 20 μg/ml.

Figure 8:
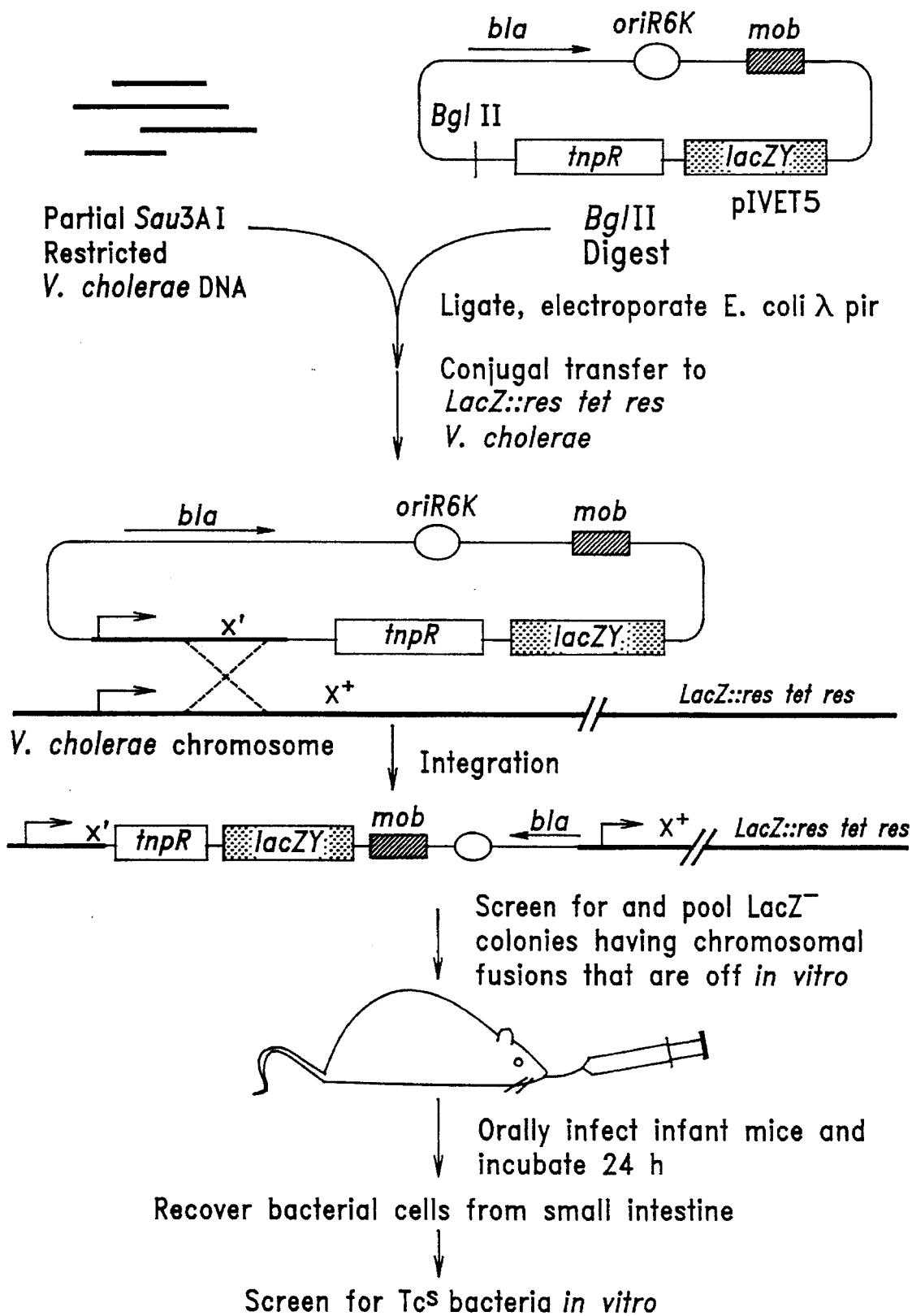
FIG. 8 is a flow sheet representing the method of screening for genes that are induced in the host using pIVET5.

Method of using pAC20 and pAC21 to Construct a V. cholerae lacZ::res1 tet res1 and a lacZ::res tet Maniatis, et al., Molecular Cloning: A Laboratory Manual, Cold Spring Harbor Laboratory, Cold Spring Harbor, N.Y. Random chromosomal fragments having Sau3A I ends were then generated by partially digesting the previously isolated genomic DNA with Sau3A I (New England Biolabs) following the manufacturer's instructions. The resulting Sau3A I partially restricted chromosomal fragments, 1–3.5 kbp in size were purified from an agarose gel after electrophoresis separation using standard methods (T. Maniatis, et al., Molecular Cloning: A Laboratory Manual, Cold Spring Harbor Laboratory, Cold Spring Harbor, N.Y.), prior to ligation in the pIVET5. As shown in FIG. 8 ligation of the Sau3A I DNA fragments with the pIVET5 vectors was achieved by standard methods producing the pIVET5 fusions. (T. Maniatis et al., Molecular Cloning: A Laboratory Manual, Cold Spring Harbor Laboratory, Cold Spring Harbor, N.Y.).

These pIVET5 fusions were then electroporated into competent E. coli cells from strain SM10λ pir (V. Miller et at., J. Bacteriol. 170:2575, 1988) to create a pool of tnpR fusions. E. coli SM10λ pir is available from Dr. J. Mekalanos Department of Microbiology and Molecular Genetics, Harvard Medical School, 200 Longwood Avenue, Boston, Mass. 02115 and Dr. V. DiRita Department of Microbiology and Immunology, University of Michigan Medical School, Ann Arbor, Mich. 48109.

Electroporation was carded out with a BioRad Gene Pulser apparatus Model No. 1652098. E. coli SM10λ pir cells were prepared for electroporation as per the manufacturer's instructions. An aliquot of cells was mixed with an aliquot of pIVET5 fusions and placed on ice for 1 minute. The mixture was transferred into a cuvette-electrode (1.9 cm) and pulsed once at a field strength of 12.5 kV/cm as per manufacturer's instructions. The mixture was then added to 1 ml SOC medium (2% tryptone, 0.5% yeast extract, 10 mM NACl, 25 mM KCl, 10 mM $MgCl_2$, 10 mM $MgSO_4$, 20 mM glucose) and shaken at 37° C. for one hour. Transformed bacteria were selected on L-agar media supplemented with Ap, 100 μg/ml.

The transformed E. coli SM10λ pir cells were then used to introduce the pIVET fusions into V. cholerae strains C6709-1 and 0395, which both lack the pir gene and are streptomycin-resistant, following the procedures described by J. Miller, A Short Course in Bacterial Genetics: a laboratory manual and handbook for *Escherichia coli* and related bacteria, Cold Spring Harbor Press, Cold Spring Harbor, N.Y., (1992). Exconjugates of V. cholerae were selected on L-agar media supplemented with Ap, 50 μg/ml and Sm, 100 μg/ml as discussed below. The Sm was added to counterselect the E. coli donor bacterial cells. Those V. cholerae which survive in the presence of ampicillin must have the pIVET5 fusion integrated into their genome by way of homologous recombination with the cloned Sau3A I V. cholerae DNA. This results in single copy diploid fusions in which one promoter drives the expression of the tnpR fusion and the other promoter drives the expression of the wild type gene.

There are several important points about this integration event. First, the cloned Sau3A I chromosomal fragments provide the only site of homology for integration into the recipient chromosome. Also, the lac regions of the pIVET5 vector are not homologous to the lac region on the chromosome of the V. cholerae strain. Second, only those clones that contain the 5'-end of the gene of interest, i.e., the promoter, will generate both a functional fusion and a duplication that maintains transcription of the wild type gene. Other types of clones will not result in the desired product. For example, those constructs that contain an internal fragment of the gene will generate a fusion, encoded by the synthetic operon, under the appropriate regulation, but will disrupt the expression of the wild type gene. This type of construct can potentially be selected against in the animal if the product of the wild type gene is required for the infection process. In other cases, the promotor will not be in the proper orientation to drive the expression of tnpR. Therefore, integration of the cloned fragment into the chromosome does not result in a functional fusion.

The subsets of the exconjugates from both matings that had transcriptionally inactive fusions to tnpR lacZY in vitro, i.e., exhibited an $Ap^r$, $LacZ^-$ phenotype on LB agar, were then screened for as described below. Dilutions of the El Tor and 0395 V. cholerae matings stored at –70° C. were plated on LB agar supplemented with Sm, 100 μg/ml; Ap, 50 μg/ml; and X-gal, 40 μg/ml. The plates containing El Tor and 0395 V. cholerae (J. Mekalanos, 1983, Cell 35:253–263) were incubated for 20 hours at 37° C. and 30° C., respectively. The exconjugates from each mating selected for by growth on these plates formed individual colonies exhibiting a broad spectrum of blue color intensity (from dark blue to very light blue) due to differing levels of Latz activity mediated by different transcriptional activities of gene fusions to tnpR lacZY. The level of Latz activity in individual colonies, visually determined on these plates, corresponded well with loss of tetracycline-resistance due to resolution mediated by the transcriptionally active fusions to tnpR lacZY. This was shown by testing for loss of tetracycline-resistance of many individual colonies of varying Latz activities and finding that most dark blue colonies were $Tc^s$, some blue colonies were $Tc^s$, and no light blue colonies were $Tc^s$. Thus, pools of 100 light blue exconjugate colonies, having inactive fusions to tnpR lacZY in vitro, were collected by patching with sterile toothpicks onto LB agar plates supplemented with Sm, 100 μg/ml; Ap, 50 μg/ml; and Tc, 2 μg/ml. The plates were incubated at 37° C. for approximately four hours, then each pool was collected from each plate by suspending the bacteria in 0.5 ml LB broth. Each pool was then stored at –70° C. in 50% LB broth and 50% glycerol.

Figure 9:
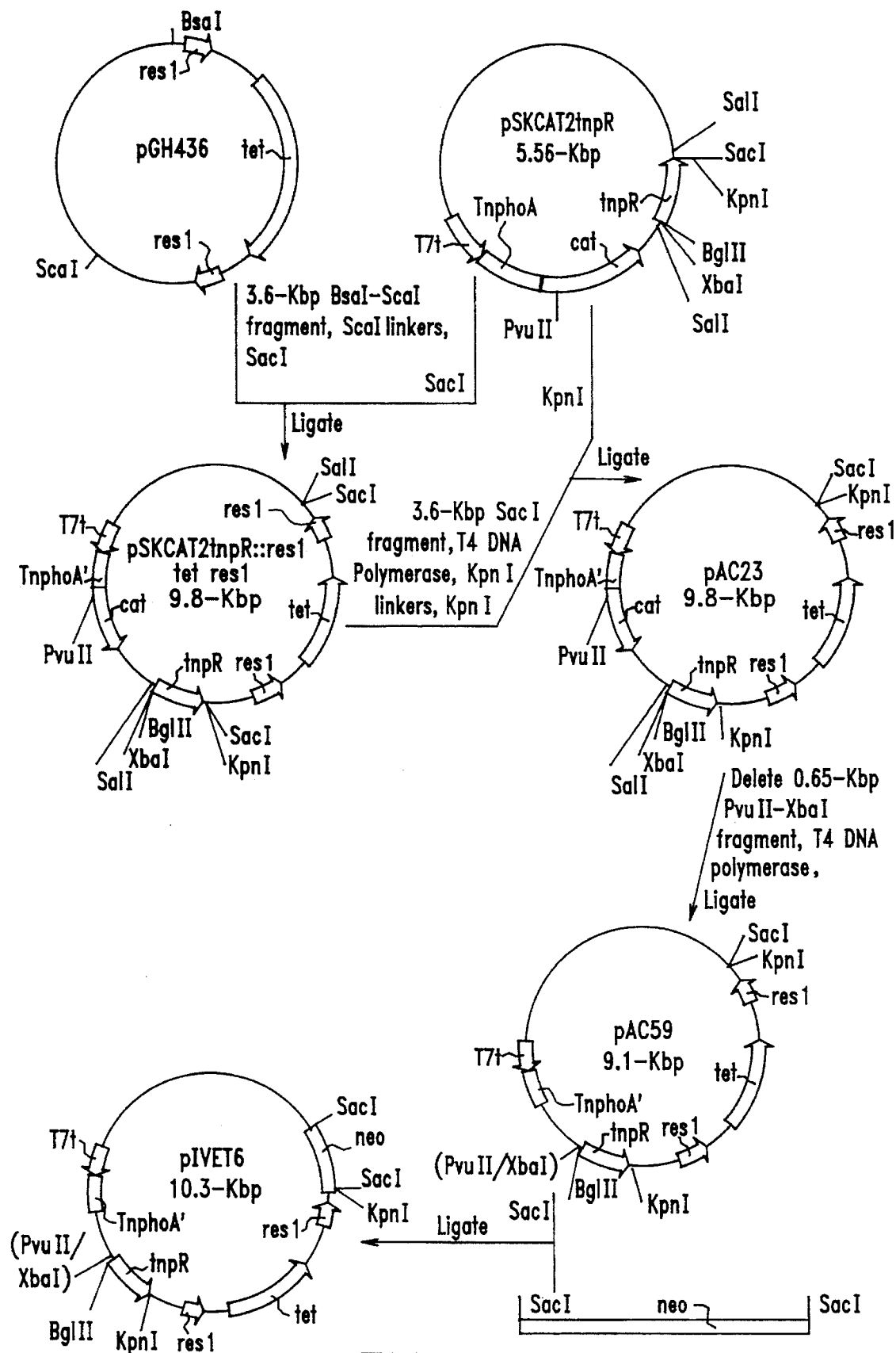
FIG. 9 is a diagrammatic representation of the construction of the pIVET6 vector.

Each pool stored at –70° C. was used to inoculate 2 ml LB supplemented with Sm, 100 μg/ml; Ap, 50 μg/ml; and Tc, 2 μg/ml, and the cultures were grown to stationary-phase overnight at 30° C. with aeration. For oral inoculations of infant mice, a 0.1 ml aliquot of each culture was washed three times in 1 ml and diluted 2000-fold in 0.15M NaCl. Eight microliters of blue food coloring (SCM Corporation, Salem, Mass.) was added per ml of diluted bacteria and, 5-day-old suckling CD-1 mice (Charles River Breeding Labs, Inc., Wilmington, Mass.), lightly anesthetized with ether, were orally infected with 50 μl, representing approximately $1 \times 10^5$ CFU. Oral infections were done by inoculating directly into the stomach using thin polyethylene tubing (PE10; Clay Adams, Parsippany, N.J.) connected to a 30G1/2 needle on a 1 ml syringe (Becton Dickinson, Franklin Lakes, N.J.). Proper inoculation of bacteria into the stomach was verified by visualizing the blue dye in the stomach externally through the infant mouse skin. The mice were separated from their mothers, put in a 30° C. humidified incubator, and sacrificed by cervical dislocation after 24 hours. Homogenates of the portion of the small intestine from 1 cm above the cecum extending to 1 cm below the stomach were made in 5 ml LB broth on ice using a mechanical homogenizer (Biospec Products, Bartlesville, Okla.). During colonization and growth within the infant mouse small intestine, it is hypothesized that transcription of many V. cholerae genes will be induced, a subset of which will be important for virulence and/or pathogenesis of *V. cholerae* in this animal model of infection. Induction of any gene that was transcriptionally fused to the synthetic tnpR lacZY operon will result in resolution or excision of the resolvase substrate res tet res (or res1 tet res1 for 0395 *V. cholerae*) allowing isolation of this subset of bacterial clones due to their $Tc^s$ phenotype. Thus, the $Tc^s$ bacteria recovered from the mouse small intestines were screened for by replica plating. Colonies were grown on LB agar and replica-plated onto LB agar supplemented with 2 μg/ml Tc; the replica plates were incubated at 37° C. and the $Tc^s$ colonies were enumerated after eight hours. $Tc^s$ bacteria were found at a frequency of approximately 0.5%, 1/200 bacteria screened. One or more $Tc^s$ bacteria were isolated from six of the sixteen pools that were passaged in infant mice.

As a negative control, it was shown that a 24 hour mouse infection with the parental El Tor *V. cholerae* lacZ: :res tet res strain, which contained no tnpR fusion, resulted in no loss of tetracycline-resistance. In addition, mouse passages of several pure clones of both El Tor and 0395 *V. cholerae* that had inactive fusions in vitro, resulted in no loss of tetracycline-resistance. Thus, the $Tc^s$ bacterial clones recovered from the mouse-passaged pools each contain chromosomal gene fusion to tnpR lacZY that were transcriptionally active at some time and place during the mouse infection.

Identifying the In Vivo Induced Genes

In order to identify the in vivo expressed genes, the integrated pIVET5 fusion plasmids from each $Tc^s$ bacterial clone were directly recovered as follows. Integration of the pIVET5 recombinant plasmids into the *V. cholerae* chromosome is a reversible reaction; thus, the integrated plasmid excises at a low frequency. The excised pIVET5 derivatives were directly recovered by isolating the plasmid DNA from 40 ml LB broth cultures supplemented with Ap, 50 μg/ml of each $Tc^s$ bacterial clone using Qiagen miniprep columns (Qiagen Inc., Chatsworth, Calif. 91311) according to the manufacturer's instructions. The recovered plasmid DNA was electroporated into *E. coli* DH5αλpir as previously described. Transformed bacteria were selected on LB agar supplemented with Ap, 60 μg/ml. Plasmid DNA was prepared from a single *E. coli* transformant derived from each original $Tc^s$ *V. cholerae* clone using standard methods (T. Maniatis, et al., Molecular Cloning: A Laboratory Manual, Cold Spring Harbor Laboratory, Cold Spring Harbor, N.Y.), and restriction digests were performed to confirm the expected structure of the pIVET5 derivatives. These seven pIVET5 derivatives were derived from five of the original six bacteria pools passaged in infant mice.

Using a primer, homologous to the 5'-end of the tnpR gene approximately 200 to 400 base pairs of *V. cholerae* DNA immediately 5' to the tnpR gene in each of the seven derivatives were sequenced using an Applied Biosystems Model 373A DNA sequencer (Applied Biosystems Inc., Foster City, Calif. 94404) according to the manufacturer's instructions. Comparisons of the predicted amino-acid sequences of the sequenced partial open reading frames that were transcriptionally fused to tnpR with sequences in the GCG non-redundant protein database (Searched Jul. 4 14:35:36 EDT 1993; Genetics Computer Group Inc., 1991, Version 7.2, Madison, Wis. 53711) were done using the Blast algorithm (National Center for Biotechnology Information BLAST Network Service). Three of the seven fusions were in genes encoding proteins that showed no significant homology to sequences in the database. This suggests that the in vivo expression technology system based on pIVET5 has identified previously uncharacterized genes that are induced during mouse infection.

The remaining four fusions were in genes encoding proteins highly homologous to three different *E. coli* and one *Bacillus subtills* protein; Amino-acid acetyl transferase, Tyrosine-specific transport protein, Oxoglutarate dehydrogenase (lipoamide), and Surfactin synthetase, respectively. The importance for virulence of *V. cholerae* in the infant mouse model of infection of the seven in vivo expressed genes identified using pIVET5 is at present not known.

The seven unique pIVET5 derivatives purified above were moved back into the *V. cholerae* reporter strains, E1Tor *V. cholerae* lacZ: : res tet res and 0395 *V. cholerae* lacZ:: res1 tet res1, to regenerate the original fusion strains having unresolved reporter aileles. These were examined for LacZ activity in vitro after growth on LB agar supplemented with Ap, 60 μg/ml and X-gal, 40 μg/ml, and were found to have light blue colony colors indicating that all seven fusions to tnpR lacZY were transcriptionally inactive in vitro as expected. Construction of these strains has allowed examination of resolution of each pure clone in vivo during infection of infant mice. The bacterial strains were prepared and used to infect mice as above. Bacteria were recovered from the mice small intestines after 24 hours and screened for loss of tetracyclineresistance as described above. All seven strains gave rise to $Tc^s$ progeny during mouse passage confirming that each chromosoma gene fusion to tnpR lacZY was transcriptionally active during infection of infant mice.

EXAMPLE 2

Construction of pIVET6

Plasmid pIVET6 as shown in FIG. 9 was constructed as follows. Plasmid pIVET6 is a derivative of pSKCAT2 tnpR, described previously in Example 1. A 3.6-kbp Bsa I and Sca I fragment containingres1 tet res1, "res1 tet res1" refers to the tet gene flanked by direct repeats of the 120-bp res1 DNA sequence, was isolated from pGH436 (Stark, W. M., et al. 1991, *EMBO* 10:3541–3548); available from Dr. J. Mekalanos and Dr. G. Hatfull, Sac I linkers (New England Biolabs) were added and, the resulting fragment was digested with Sac I and inserted into the Sac I site of pSKCAT2tnpR to generate pSKCAT2tnpR::res1 tet res1. Subsequently, the 3.6-kbp Sac I fragment containing res1 tet res1 was isolated from pSKCAT2tnpR::res1 tet res1, the DNA ends were filled-in with T4 DNA polymerase, Kpn I linkers (New England Biolabs) were added, and the resulting fragment was digested with Kpn I and inserted into the Kpn I site of pSKCATtnpR to generate pAC23. Due to high background resolution in a recombinant plasmid constructed earlier using the wild-type res sequences, we substituted mutant res1 sequences which are recombined by resolvase at a level approximately 10% that of wild-type res sequences (Stark, W. M., et al. 1991, *EMBO* 10:3541–3548).

The cat gene was deleted from pAC23 on a 0.65-kbp Pvu 1I and Xba I fragment followed by a filling-in of the DNA ends with T4 DNA Polymerase and self-ligation, resulting in pAC59.

Lastly, a 1.165-kbp Hind III and Bst BI fragment containing the neogene of Tn5 (Beck, E., et al., 1982, *Gene* 19:327–336) had its DNA filled-in using T4 DNA Polymerase, Sac I linkers (New England Biolabs) were added, and the fragment was digested with Sac I and inserted into the Sac I site of pAC59 such that the direction of neo transcription was the same as that of the TnphoA' partial sequence on pAC59, to generate pIVET6 as shown in FIG. 9. pIVET6, as shown in FIG. 10, can be used to replace internal TnphoA sequences, by allelic exchange, with sequences on pIVET6 flanked by TnphoA 5' and 3' sequences. pIVET6 was electroporated into *Escherichia coli* DH5αλpir (Hanahan, D., 1983, *J. Mol. Biol.* 166:557–580; Kolter, R., et al., 1978, *Cell* 15:1199–1208) using a Bio-Rad Gene Pulsar apparatus Model No. 1652098 (Bio-Rad Laboratories, 1414 Harbour Way S., Richmond, Calif. 94804) following the manufacturer's instructions. The genotype of this strain is not relevant except that it is RecA$^-$ and Pir$^+$. pIVET6 was maintained in *E. coli* by growth on LB (Davis, R. W., et al., 1980 in Advanced Bacterial Genetics, Cold Spring Harbor Laboratory, Cold Spring Harbor, N.Y.) agar supplemented with ampicillin (Ap), 50 µg/ml; tetracycline (Tc), 3 µg/ml; and kanamycin (Km), 20 µg/ml. pIVET6 was also electroporated in *E. coli* SM10λpir (Miller, V. & Mekalanos, J. J., 1988, *J. Bacteriol.* 170:2575–2583). The genotype of this strain is not relevant except that it is RecA$^-$, Pit$^+$ and has RP4-2-Tc::Mu integrated into its chromosome which provides P-group transfer functions for mobilization of pIVET6 into other bacteria as discussed in further detail below.

Method of using pIVET6 to Convert a *Bordetella peaussis* vrg6::TnphoA Gene Fusion into a vrg6::tnpR Gene fusion by Allelic Exchange

*B. pertussis* is a human respiratory bacterial pathogen which causes whooping cough. In a process termed antigenie modulation, the expression of many known virulence factors of *B. pertussis* are repressed during growth in the presence of "modulating" chemicals such as MgSO$_4$ and nieotinate (Lacey, B. W., 1960, J. Hyg. 58:57–93; Pusztai, Z. & Joo, I., 1967, *Ann. Immunol. Hung.* 10:63–70). However, some B. pertussis virulence factors show a reciprocal mode of regulation and are maximally expressed under modulating growth conditions (Knapp, S. & Mekalanos, J. J., 1988, *J. Bacteriol.* 170:5059–5066). One example is the vrg6 gene whose expression, as monitored by alkaline phosphatase activity levels of a Vrg6-PhoA fusion protein in *B. pertussis* strain (vrg6::TnphoA), was induced from essentially background PhoA activity levels in non-modulating growth conditions to a level of activity approximately 30-fold higher in media that contained the modulating chemicals MgSO$_4$ and nicotinate (Beattie, D. T., et al., 1990, *J. Bacteriol.* 172:6997–7004). To demonstrate that the products of genetic recombination mediated by gene fusions to resolvase could serve as a reporter of gene expression, pIVET6 was used to convert the vrg6::TnphoA translation fusion in a *B. pertussis* strain SK6 (not shown) into a transcriptional fusion to tnpR and then examined expression of the gene fusion as described in detail below.

Plasmid pIVET6 is a derivative of pSKCAT and is therefore mobilizable by broad-host-range IncP conjugative functions (Simon, R., et al., 1983, *Biotechnology* 1:784–791) and, contains oriR6K which requires the pir gene product in trans for replication Kolter, R., et al., 1978, *Cell* 15:1199–1208). Allelic exchange of the TnphoA insertion present in the vrg6 gene of *B. pertussis* SK6 for the portion of pIVET6 flanked by TnphoA sequences, i.e., TnphoA' and neo, was accomplished as follows. pIVET6 was mobilized into *B. pertussis* SK6 by biparental mating with SM10λpir (pIVET6) at a donor to recipient ratio of 1:3 on Bordet-Gengou (BG) agar (Beeton Dickinson Microbiology Systems, Cockeysville, Md. 21030) supplemented with 1% glycerol (vol/vol) and 20% defibrinated sheep's blood (vol/vol) (Adams Scientific, West Warwick, R.I.) at 36° C. for eight hours. *B. pertussis* does not contain the pir gene and thus pIVET6 can only be maintained in exconjugates by integrating into the chromosome by homologous recombination via TnphoA sequences present on pIVET6 and on the chromosome. Exconjugates were selected by growth on BG-blood agar supplemented with streptomycin (Sm), 100 µg/ml; KM, 30 µg/ml; Ap, 50 µg/ml; and Tc, 0.8 µg/ml. The alkaline phosphatase negative (PhoA$^-$) exconjugates in which pIVET6 had integrated by homologous recombination between the TnphoA' sequence on pIVET6 and the 5' end of TnphoA on the B. pertussis SK6 chromosome were then screened for as previously described (Knapp, S. & Mekalanos, J. J., 1988, *J. Bacteriol.* 170:5059–5066). Allelic exchange was then completed for one PhoA$^-$ exconjugate by allowing the integrated plasmid to excise from the chromosome by homologous recombination via neo sequences during three days of growth on BG-blood agar at 36° C. The rare PhoA$^-$, streptomycin-resistant (Sm$^r$), kanamycin-resistant (Km$^r$), tetracycline-resistant (Tc$^r$), ampicillin-sensitive (Ap$^s$) allelic exchange routants were screened for by patching several hundred individual colonies. One such clone was designated strain AC-B121.

Method of using pIVET6 to Study In Vitro Expression of the vrg6 Gene of *Bordetella pertussis*

AC-B121 was grown on BG-blood agar supplemented with Sm, 100 µg/ml; Km, 30 µg/ml; and Tc, 0.8 µg/ml. Approximately 1000 colonies were scraped-up and streaked heavily using a sterile wooden inoculating stick onto BG-blood agar and onto BG-blood agar supplemented with 20 mM MgSO$_4$ and 5 mM nicotinate (modulating conditions) and the plates were incubated at 36° C. in a humidified incubator. Resolution within the bacteria and subsequent dilution of the excised tet mini-circles during multiplication on the agar plates should result in Tc$^s$ bacterial progeny. Therefore, the percentage of the bacterial population from each plate that was Tc$^s$ served as a measure of prior resolution and thus transcriptional expression of the tnpR gene fusion during growth on the two media. Therefore, at timepoints of 0, 1, 2, 3, and 4 days after inoculating the plates, moderate portions of sector II growth, representing many thousands of colonies, were scraped-up from each plate and streaked for single colonies onto BG-blood agar supplemented with Sm, 100 µg/ml; Km, 30 µg/ml. After three days of growth at 36° C. in a humidified incubator, the percent of the population that was Tc$^s$ was determined as follows. Approximately 160 colonies from each timepoint were individually patched onto BG-blood agar supplemented with Sm, 100 µg/ml; Km, 30 µg/ml; and Tc, 0.8 µg/ml; the plates were incubated at 36° C. in a humidified incubator, and growth or lack of growth of the colony-patchings were scored after 48 hours.

As shown in FIG. 12, growth of AC-B121 on BG-blood agar (non-modulating conditions) resulted in a steady low level of resolution or excision throughout the 4 day experiment (<3% Tc$^s$ bacteria). However, growth in the presence of modulators resulted in a time-dependent linear increase in the Tc$^s$ fraction of the bacterial population which approached 100% after four days of growth. Thus the vrg6-tnpR fusion was induced in the presence of the modulators MgSO$_4$ and nicotinate resulting in resolution of the tet reporter gene from the bacterial chromosomes. In contrast to the rapid and complete resolution followed by rapid bacterial multiplication which was observed in next example below (>99% Tc$^s$ for *Vibrio cholerae* AC-V88 after eight hours of logarithmic growth), the Tc$^s$ fraction of the *B. pertussis* AC-B 121 population on BG-blood agar plus modulators was limited both by slow multiplication (~8 hours doubling time) and by the rate of resolution which was calculated to have been between 0.2–0.4 cointegrates resolved per cell per generation.

Method of using pIVET6 to Study In Vivo Expression of the vrg6 Gene of *Bordetella pertussis*

*B. pertussis* strain SK6 (vrg6::TnphoA) was shown to have attenuated virulence in a murine model of infection (Beattie, D. T., et al., 1992, *Infect. Immun.* 60:571–577), and to exhibit reduced survival inside tissue culture cells of a murine macrophage-like cell line compared to the wild-type strain (Beattie, D. T. and J. J. M., unpublished dam). These data suggested that the *B. pertussis* vrg6 gene was expressed after phagocytosis into tissue-culture macrophages; a phenomenon that may take place within host lung macrophages allowing increased intracellular survival during infection. To demonstrate that the products of genetic recombination mediated by gene fusions to resolvase could serve as a reporter of microbial gene expression within host cells in tissue culture, the vrg6-tnpR fusion strain AC-B12 1 was used as a reporter of vrg6 gene expression after phagocytosis into a murine macrophage-like cell line.

AC-B121 was swabbed onto BG-blood agar supplemented with Sm, 100 μg/ml; Km, 30 μg/ml; and Tc, 0.8 μg/ml and grown at 36° C. in a humidified incubator for three days. Bacterial cells were scraped-up and resuspended in Stanier-Scholte broth (Kloss, W. E., et al., 1979, In C. R. Manelark and J. C. Hill [ed.], International Symposium on Pertussis. U.S. Department of Health, Education, and Welfare, Washington, D.C., pp. 70–80) to approximately 1×10$^{10}$ CFU/ml using a previously made standard curve of CFU/ml versus optical density at 600 nm wavelength to calculate the correct concentration. The bacterial suspension was then pelleted in a microcentrifuge and the bacterial pellet resuspended in tissue culture media, as described in further detail below, to the original volume (to preserve the concentration of 1× 10$^{10}$ CFU/ml). This bacterial suspension was used to infect tissue culture cells as described below.

Two days before the infection experiment was performed, monolayers of the J774A.1 macrophage-like cell line (ATCC TIB 67) were layed down as follows: 1×10$^5$ J774A.1 cells were suspended in 2 ml of MEM media (Gibco BRL, Grand Island, N.Y. 14072-0068) supplemented with 10% heat-activated calf serum (Gibco BRL), 1×L-glutamine (Bio Whittaker Inc., Walkersville Md. 21793) and 1x penicillin-streptomycin (Bio Whittaker), and were aliquoted into each well in a 6-well tissue culture dish (Costar, Cambridge, Mass. 02140). The monolayers were grown to confluency at 37° C. in a humidified 5% CO$_2$ atmosphere for approximately two days. Prior to infection of the monolayers with bacteria, the media was removed, the monolayers were gently washed three times with 37° C. phosphate-buffered saline (PBS; 137 mM NaCl, 2.7 mM KCl, 5.4 mM Na$_2$HPO$_4$, 1.8 mM KH$_2$PHO$_4$, pH7.4), and fresh media without antibiotics was added to the monolayers. Each well containing approximately 1×10$^6$ J774A.1 cells, or media alone control wells, was infected with 1×10$^8$ *B. pertussis* AC-B121 CFU by aliquoting 10 μl of the bacterial suspension prepared above directly into the media and swirling to distribute the bacterial cells. After one hour at 37° C. in a humidified 5 % CO$_2$ atmosphere, non-adherent bacteria from the wells containing J774A.1 cells were removed by gently washing the monolayers three times with 37° C. PBS and then adding 2 ml of fresh media supplemented with 200 μg/ml polymyxin B (Sigma Chemical Co., St. Louis, Mo. 63178). The antibiotic polymyxin B was added to the monolayers to kill any extracellular bacteria (Beattie, D. T. & J. J. M., unpublished dam).

After an additional one hour, intracellular bacteria were recovered from infected monolayers by first washing the monolayers three times with 37° C. PBS to remove the polymyxin B followed by hypoosmotic lysis of the monolayer cells with 1 ml of sterile aleionized water accompanied with repeated pippetting. Serial dilutions of the recovered bacteria as well as bacteria from the media alone control, were plated onto BG-blood agar supplemented with Sm, 101 μg/ml; Km, 30 μg/ml; and the plates were incubated at 36° C. in a humidified incubator for three days. Loss of tetracycline-resistance among intracellular bacteria, mediated by induction of the vrg6-tnpR fusion, was then determined as described above for in vitro grown AC-B121. During two hours of incubation in tissue culture media alone, a very low level of resolution occurred as shown by a slight loss of tetracycline-resistance, 3 % Tc$^s$, as shown in Table 1 below.

TABLE 1

| Environment | % Tc$^S$* |
|---|---|
| Tissue culture media | 3 $^+/_-$ 2 |
| J774A. 1 cells | 24.3 $^+/_-$ 0.6 |

*Mean $^+/_-$ SD of ([Tc$^S$ CFU per ml/total CFU per ml] × 100) for three independent in vitro experiments.

However, after a two hour infection of J774A. 1 cells, approximately 24 % of the bacteria were Tc$^s$ (Table 1) demonstrating that the vrg6-tnpR fusion was induced during infection of the macrophage cells. These data show that the products of genetic recombination mediated by gene fusions to resolvase can serve as a reporter of microbial gene expression in vivo within tissue culture cell models of infection.

Method of using pIVET6 to Convert a Vibrio cholerae irgA:: TnphoA Gene Fusion into a irgA::tnpR Gene Fusion by AHelic Exchange

*V. cholerae* is a human intestinal bacterial pathogen that causes the diarrheal disease cholera. Transcription of the *V. cholerae* irgA gene has been shown to be highly regulated by available iron concentrations ([Fe$^{2+}$]) in the growth medium in vitro (Goldberg, M. B., et al., 1990, *Infect. Immun.* 58:55–60). In fact, it was found that expression of an IrgA-PhoA fusion protein in *V. cholerae* strain MBG40 (irgA:: TnphoA) was induced from essentially background PhoA activity levels in media containing excess Fe$^{2+}$ to a level of activity>800-fold higher in low [Fe$^{2+}$] media that contained the iron-chelator 2,2'-dipyridyl (Goldberg, M.B., et al., 1990, *Infect. Immun.* 58:55–60). To further demonstrate that genetic recombination mediated by gene fusions to resolvase could serve as a reporter of gene expression, pIVET6 was used to convert the irgA::TnphoA translational fusion in strain MBG40 into a transcriptional fusion to tnpR and then expression of the gene fusion was examined as described in the following section.

Figure 11:
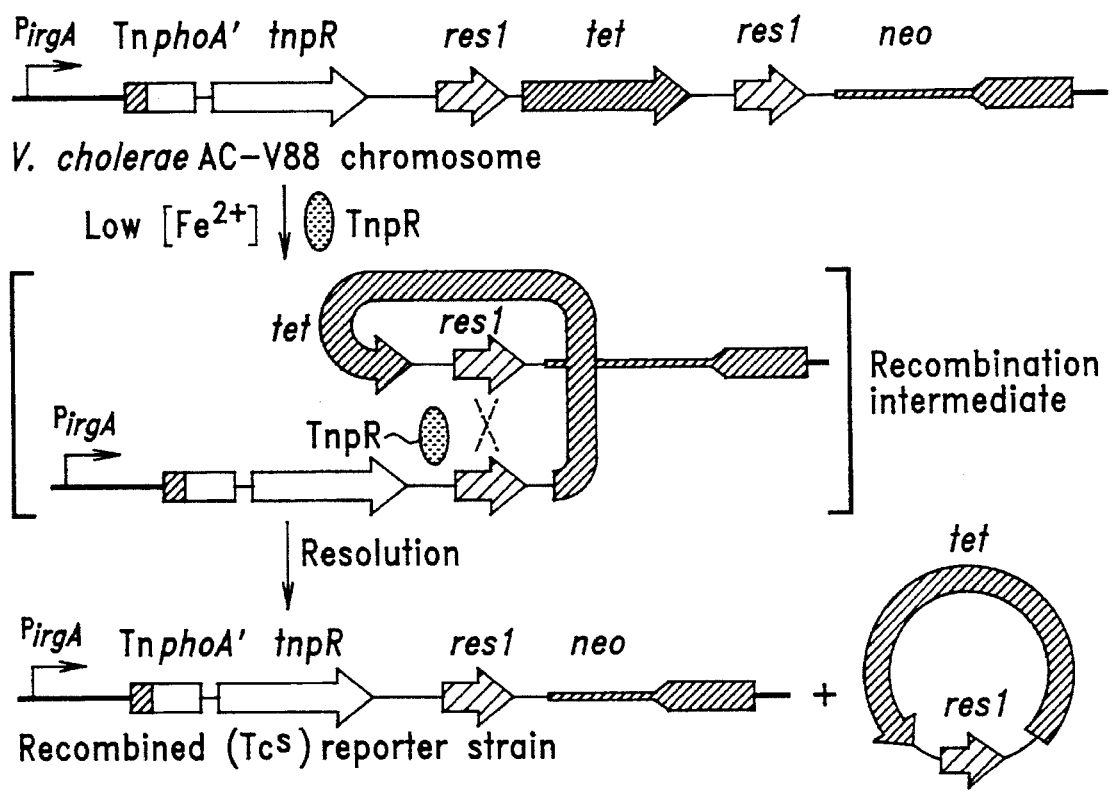
FIG. 11 is a diagrammatic representation depicting the resolution reaction mediated by resolvase protein upon induction of the irgA promoter by low [$Fe^{2+}$]

Allelic exchange of the TnphoA insertion present in the irgA gene of *V. cholerae* MBG40 (Goldberg, M.B., et al., 1990, *Infect. Immun.* 58:55–60) for the portion of pIVET6 flanked by TnphoA sequences, i.e., TnphoA' and neo, as shown in FIGS. 10 and 11, was accomplished as follows.

pIVET6 was mobilized into *V. cholerae* MBG40 by triparental mating with *E. coli* strains CSH56 (Ditta, G., et al., 1980, *Proc. Natl. Acad. Sci. USA* 77:7347–7351) and DH5αλpir (pIVET6) at an approximate cellular ratio of 1:1:1 on LB agar media at 37° C. for 10 hours. CSH56 provided conjugative transfer functions to mobilize pIVET6 from DH5αλpir (pIVET6) into *V. cholerae* MBG40. *V. cholerae* does not contain the pir gene and thus pIVET6 can only be maintained in exconjugates by integrating into the chromosome by homologous recombination via TnphoA sequences present on pIVET6 and on the chromosome. The PhoA$^-$ exconjugates in which pIVET6 had integrated by homologous recombination between the TnphoA' sequence on pIVET6 and the 5' end of TnphoA on the *V. cholerae* MBG40 chromosome were screened for on LB agar supplemented with Sm, 100 μg/ml; Km, 30 μg/ml; Ap, 50 μg/ml; Tc, 0.8 μg/ml; and the alkaline phosphatase substrate 5-bromo-4-chloro-3-indolylphosphate (X-P) (Bachem, Torrance, Calif.), 80 μg/ml. Allelic exchange was completed by allowing the integrated plasmid to excise from the chromosome by homologous recombination via neo sequences during approximately 20 generations of growth in LB broth at 30° C. The rare PhoA$^-$, Sm$^r$, KM$^r$, Tc$^r$, Ap$^s$ allelic exchange mutants were screened for by plating dilutions on LB agar supplemented with Sm, 100 μg/ml; Km, 30/μg/ml; Tc, 0.8 μg/ml; and then replicaplating onto LB agar supplemented with Ap, 50 μg/ml and X-P, 80 μg/ml. One such bacterial clone was designated strain AC-V88.

Method of using pIVET6 to Study In Vitro Expression of an Iron-regulated Gene of *Vibrio cholerae*

*V. cholerae* AC-V88 was grown overnight to stationary phase at 30° C. with aeration in LB broth supplemented with Tc, 0.8 μg/ml and 36 μM FeSO$_4$. A small aliquot of this culture was diluted 2000-fold in LB broth supplemented with either 36 μM FeSO$_4$ or with 0.1 mM of the iron-chelator 2,2'-dipyridyl (Sigma Chemical Co.) and the diluted cultures were grown for eight hours to stationary phase at 37° C. with aeration. This represented approximately 11 generations of bacterial multiplication. Resolution within the cultures and subsequent dilution of the excised tet mini-circles during bacterial multiplication resulted in Tc$^s$ bacterial progeny in the end cultures. Therefore, the percentage of the bacterial population of each end culture that was Tc$^s$ served as a measure of prior resolution and thus transcriptional expression of the tnpR gene fusion within the bacteria in the culture. The total numbers of bacterial CFU/ml of the end cultures were determined by plating serial dilutions on LB agar supplemented with Sm, Tc and 36 μM FeSO$_4$. For the cultures that contained 2,2'-dipyridyl, the numbers of Tc$^r$ CFU/ml were determined by plating serial dilutions on LB agar supplemented with Sm, Tc and 36 μM FeSO$_4$. The percentage of Tc$^s$ progeny in the end cultures was then calculated by subtracting the number of Tc$^r$ CFU/ml from the total number of bacterial CFU/ml, dividing this number (which is equivalent to the number of Tc$^s$ CFU/ml) by the total bacterial CFU/ml multiplied by 100. To accurately determine the percentages of the bacteria that were Tc$^s$ from the high [Fe$^{2+}$] end cultures, where the Tc$^r$ CFU/ml and total CFU/ml were nearly equivalent, colonies grown on LB agar supplemented with Sm and 36 μM FeSO$_4$ were replicaplated onto LB agar supplemented with Sm, 2 μg/ml Tc, and 36 μM FeSO$_4$; the replica plates were incubated at 37° C. and the Tc$^s$ colonies were enumerated after eight hours. The percentage of Tc$^s$ progeny in the end culture was then calculated by dividing the Tc$^s$ CFU/ml by the total bacterial CFU/ml multiplied by 100.

As shown in Table 2 below, growth of AC-V88 in media containing excess Fe$^{2+}$ resulted in no detectable Tc$^s$ progeny indicating that resolution had not occurred.

TABLE 2

| Growth condition | % Tc$^S$* |
| --- | --- |
| LB + 36 μM Fe$^{2+}$ | 0.7 +/− 0.4 |
| LB + 0.1 mM 2,2'-dipyridyl | 99.5 +/− 0.4 |
| Small intestine† | 1 +/− 2 |
| Peritoneal cavity†† | 62 +/− 14 |

*Mean +/− SD of ([Tc$^S$ CFU per ml]/total CFU per ml] × 100) for three independent in vitro experiments; and of the recovered bacteria from the small intestines and peritoneal cavities of six and nine animals, respectively.
†24 hour oral infection of 5-day-old CD-1 suckling mice.
††24 hour i.p. infection of 5-day-old CD-1 suckling mice.

AC-V88 was found to resolve to an intermediate level in unsupplemented LB broth demonstrating the requirement for excess [Fe$^{2+}$] to fully repress irgA transcription in LB broth. However, 11 generations of growth in a low [Fe$^{2+}$] medium containing 2,2'-dipyridyl resulted in essentially complete loss of tetracycline-resistance within the bacterial population (99.5% Tc$^s$ progeny), as previously shown in Table 2. This data suggested that resolution occurred rapidly and completely before multiplication of bacteria in the diluted culture began. (For comparison, complete resolution, i.e., complete excision of all res1 tet res1 sequences, from the chromosomes of all bacteria in a culture prior to 11 generations of subsequent bacterial multiplication should theoretically result in approximately 99.95 % Tc$^s$ progeny, where the few remaining Tc$^r$ progeny still harbor the excised tet mini-circle which is stable but non-replicating. This theoretical calculation was made by summing the Tc$^s$ and Tc$^r$ progeny expected after 11 generations of growth of a single bacterium containing a single excised tet mini-circle; which gives 2047 Tc$^s$ bacteria and 1 Tc$^r$ bacterium, or a 99.95 % Tc$^s$ population.) Thus, under defined growth conditions in vitro, the induction of tnpR expression mirrored that previously found for phoA fusion when either were fused to the *V. cholerae* irgA gene, evidencing that resolvase-mediated resolution of the cointegrate substrate, res1 tet res1, can serve as a useful reporter of heterologous gene transcription in vitro.

Method of using pIVET6 to Study In Vivo Expression of an Iron-regulated Gene of *Vibrio cholerae*

Many pathogenic microorganisms respond to extremely low iron availability in host tissues by inducing expression of iron acquisition proteins (Finkelstein, R. A., et al., 1983, *Rev. Infect. Dis.* 5:S759–S777). Indeed, *V. cholerae* has been shown to induce expression of several outer membrane proteins in vivo during infection of rabbit ligated intestinal loops that are also induced in a low iron medium in vitro (Sciortino, C. F. & Finkelstein, R. A., 1983, *Infect. Immun.* 42:990–996). To demonstrate that the products of genetic recombination mediated by gene fusions to resolvase could serve as a reporter of microbial gene expression within tissues of a host organism, we used the irgA-tnpR fusion strain AC-V88 as a reporter of in vivo gene expression.

Strain AC-V88 was grown overnight to stationary phase at 30° C. with aeration in LB broth supplemented with Tc and 36 μM FeSO$_4$. Individual five day old infant CD-1 mice were orally infected with 1×10$^5$ CFU from this culture, and bacteria were recovered from the small intestine after 24 hours as previously described in the example above. The percentages of the bacteria recovered from the intestinal homogenates that were $Tc^s$ were determined by replicaplating as described previously above.

No detectable resolution occurred within the infant mouse small intestine as shown by a negligible loss of tetracycline-resistance, as shown in Table 2 above, suggesting that the irgA-tnpR fusion was not induced in infant mice after oral challenge. To rule out the possibility that multiple mouse passages were required to detect resolution, two consecutive mouse passages were done by infecting a second set of infant mice with 50 µl of the fresh homogenates of the intestines of the first set of mice, representing approximately $10^4$ CFU, recovering the intestinal bacteria from the second set after 24 hours and, testing for $Tc^s$ progeny. A second mouse passage did not result in detectable resolution. The lack of $Tc^s$ progeny after mouse infection was not due to insufficient bacterial multiplication in vivo which would have been required to dilute-out the excised tet mini-circles, as extensive multiplication did occur in vivo. To ensure that intestine-recovered bacteria still maintained the correct genetic structure to allow resolution, several individual colonies from in vivo-passaged bacteria were tested for resolution in vitro. All clones resolved during growth in low $[Fe^{2+}]$ media with identical kinetics as had been found for the parental strain AC-V88. Thus, the irgA-tnpR fusion was not induced to a high enough level in the small intestine of infant mice to mediate resolution.

The results above suggested that the small intestine was a non-inducing environment for the AC-V88 irgA-tnpR fusion, perhaps due to a high $[Fe^{2+}]$ or other available iron source(s). Alternatively, the irgA-inducing conditions artificially generated in vitro 2,2'-dipyridyl, which chelates other metal ions in addition to iron (Moss, M. L. & Mellon, M. G., 1942, *Industr. Eng. Chem.* 14:862–865), may not have been physiologic, i.e., may not have reflected environmental conditions found within animals, small intestine or otherwise. Previous studies have demonstrated that the peritoneal cavities of guinea pigs and rabbits are inducing environments for iron-regulated genes of E. Coli (Griffiths, E., et al., 1978, *Infect. Immun.* 22:312–317). Therefore, to demonstrate that the irgA-tnpR fusion was capable of being induced in vivo, resolution of AC-V88 in the peritoneal cavity of infant mice was examined as described below.

Intraperitoneal (j.p.) infections of infant mice were done as follows: 0.1 ml of a stationary-phase culture of AC-V88, prepared as above, was washed three times and diluted 4-fold in 0.15M NaCl. Five-day-old suckling CD-1 mice were lightly anesthetized with ether and infected i.p. with 25 µl of the diluted bacteria, representing approximately $7\times10^6$ CFU, using a 30G1/2 needle on a 1 ml syringe. The mice were separated from their mothers and put in a 30° C. humidified incubator. The mice were sacrificed after 24 hours and the bacteria were recovered from the peritoneal cavity as follows: 70 µl of LB broth supplemented with 36 µM $FeSO_4$ was injected into the peritoneal cavity followed by the withdrawal of approximately 90 µl of peritoneal fluid using a 30G1/2 needle on a 1 ml syringe. The percentages of the bacteria recovered from the peritoneal cavities that were $Tc^s$ were determined by replica-plating as outlined above. Extensive resolution occurred within the peritoneal cavity, as shown in Table 2 above, demonstrating that the irgA-tnpR fusion was capable of being induced in vivo. These data show that the products of genetic recombination mediated by gene fusion to resolvase can serve as a reporter of microbial gene expression in vivo within different host compartments.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

DEPOSITS

The following deposits were made on Sep. 22, 1993, with the American Type Culture Collection (ATCC), where the deposits were given the following accession numbers:

| Deposit | Accession No. |
| --- | --- |
| E. coli (pAC 20) AC-E20 | 69437 |
| E. coli (pAC 21) AC-E21 | 69438 |
| E. coli (PIVET6) AC-E94 | 69439 |
| E. coli (PIVET5) AC-E100 | 69440 |

Applicants' assignee, President and Fellows of Harvard College, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R. 1.14 and 35 U.S.C. 122. The deposited material will be maintained with all the care necessary to keep it viable and uncontaminated for a period of at least five (5) years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

The embodiments of the invention in which an exclusive property or privilege is claimed are defined as follows:

1. A method of detecting induction of gene expression in a microorganism during in vivo infection of a host, comprising the steps of:

(a) constructing a reporter strain or pool of reporter strains of said microorganism containing an artificial cointegrate comprising a reporter gene flanked by directly repeated recombination sequences and said microorganism further contains coding sequence under the control of a promoter sequence of said microorganism, wherein expression of said coding sequence produces a resolvase enzyme capable of resolving said cointegrate;

(b) infecting said host with said pool of reporter strains;

(c) harvesting from said host the reporter strains that survive and propagate in said host after step (b); and (d) detecting expression of said coding sequence by detecting resolution of said cointegrate thereby resulting in the loss of said reporter gene.

2. The method of claim 1, wherein said microorganism is sensitive to an antibiotic.

3. The method of claim 2, wherein said reporter gene encodes a resistance conferring protein, the expression of which is essential for the survival of said microorganism that is sensitive to said antibiotic in the presence of said antibiotic.

4. The method of claim 3, wherein resolution of said cointegrate conferring resistance to said antibiotic is detected by growing said harvested strains on a first media that lacks said antibiotic and then replica plating said growing strains onto a second media that contains said antibiotic.

5. The method of claim 1, wherein said artificial cointegrate and said coding sequence are located in the chromosomal DNA of said microorganism.

6. The method of claim 1, wherein said artificial cointegrate and said coding sequence within said microorganism are maintained on an autonomously replicating plasmid.

7. A method of detecting induction of gene expression in a microorganism during in vivo infection of a host comprising the steps of:
(a) isolating and fragmenting total chromosomal DNA of a first microbe, said first microbe being a microbial strain of a virulent microorganism sensitive to a first antibiotic;
(b) cloning the chromosomal fragments resulting from step (a) into an expression plasmid to create a library of reporter plasmids, wherein said expression plasmid comprises:
  (1) a gene conferring resistance to a second antibiotic,
  (2) a promoterless synthetic operon comprising two genes, wherein the first gene encodes a resolvase enzyme capable of resolving a cointegrate and the second gene produces a detectable product, and
  (3) a cloning site 5' to said synthetic operon, wherein said cloning step fuses a chromosomal fragment to the 5' end of the promoterless synthetic operon, and wherein the chromosomal fragment provides the only region of the reporter plasmid capable of homologous recombination with the genome of the first microbial strain;
(c) amplifying said library of reporter plasmids resulting from step (b) by introducing the reporter plasmids into a second microbial strain which provides a replication protein required for autonomous replication of said reporter plasmids;
(d) transferring said reporter plasmids into a third microbial strain under conditions where the reporter plasmids may integrate by homologous recombination at the site of homology provided by the cloned chromosomal fragments to create a pool of reporter strains, wherein said third microbial strain being said microbial strain of the virulent microorganism sensitive to said first antibiotic and the genome of said third microbial strain further carries said cointegrate wherein said cointegrate comprises a reporter gene encoding a resistance conferring protein to said first antibiotic flanked by directly repeated recombination sequences;
(e) exposing said reporter strains resulting from step (d) to said second antibiotic, to select a pool of reporter strains exhibiting integration of said fusion plasmids by homologous recombination;
(f) infecting said host with the pool of selected reporter strains resulting from step (e);
(g) harvesting from said host the reporter strains that survive and propagate within said host infected in step (f);
(h) growing said recovered microorganisms on a media which lacks said first antibiotic;
(i) transferring by replica plating said growing microorganisms resulting from step (h) onto a media that contains said first antibiotic; and
choosing those microorganisms growing in step (h) that are unable to grow in step (i).

8. The method of claim 7, wherein said expression plasmid is a suicide vector.

9. A method for detecting induction of expression of a gene in a microorganism during in vivo infection of host comprising the steps of:
(a) constructing a strain or a pool of reporter strains of said microorganism containing:
  (1) an artificial cointegrate comprising a reporter gene flanked by directly repeated recombination sequences that are further flanked by an upstream segment of a first gene fused to a promoterless second gene and a downstream segment of said first gene, wherein said upstream and downstream segments of said first gene provide sites for allelic exchange with the chromosomal DNA of said microorganism, and said promoterless second gene encodes a resolvase enzyme capable of resolving said cointegrate;
(b) infecting said host with said pool of reporter strains;
(c) harvesting from said host said reporter strains that survive and propagate in said host after step (b); and
(d) detecting expression of said second gene by detecting resolution of said cointegrate resulting in loss of said reporter gene.

10. The method of claim 9, wherein said first gene is TnphoA.

11. A method of detecting induction of gene expression in a microorganism during in vivo infection of a host comprising the steps of:
(a) isolating and fragmenting total chromosomal DNA of a first microbe, said first microbe being a microbial strain of a virulent microorganism sensitive to a first antibiotic;
(b) cloning the chromosomal fragments resulting from step (a) into an expression plasmid to create a library of reporter plasmids, wherein said expression plasmid comprises:
  (1) a gene conferring resistance to a second antibiotic,
  (2) a promoterless synthetic operon comprising two genes, wherein the first gene encodes a resolvase enzyme capable of resolving a cointegrate comprising a reporter gene flanked by directly repeated recombination sequences and the second gene encodes a detectable product, and
  (3) a cloning site 5' to said synthetic operon, wherein said cloning step fuses a chromosomal fragment to the 5' end of the promoterless synthetic operon, and wherein the chromosomal fragment provides the only region of the reporter plasmid capable of homologous recombination with the genome of the first microbial strain;
(c) introducing said reporter plasmids into a second microbial strain thereby creating reporter strains, such that said reporter plasmids are autonomously maintained within said second microbial strain, wherein said second microbial strain being said microbial strain of the virulent microorganism sensitive to said first antibiotic, and wherein said reporter gene encodes a resistance conferring protein to said first antibiotic;
(d) exposing said reporter strains resulting from step (c) to said second antibiotic to select a pool of reporter strains exhibiting maintenance of said fusion plasmids
(e) infecting said host with the pool of selected reporter strains of step (d);
(f) harvesting from said host the reporter strains that survive and propagate within said host infected in step (e);
(g) growing said harvested microorganisms on a media which lacks said first antibiotic;
(h) transferring by replica plating said growing microorganisms resulting from step (g) onto a media that contains said first antibiotic; and
(i) choosing those microorganisms growing in step (g) that are unable to grow in step (h).

12. A method of detecting induction of gene expression in a microorganism during in vivo infection of a host, comprising the steps of:

(a) constructing a reporter strain or pool of reporter strains of said microorganism containing an artificial cointegrate comprising direct repeats of a specific res sequence flanking a reporter gene, and further containing a synthetic operon under the control of a promoter sequence of said microorganism, wherein said synthetic operon encodes (1) a resolvase enzyme capable of resolving said cointegrate and (2) a detectable marker;

(b) infecting said host with said pool of reporter strains;

(c) harvesting from said host said reporter strains that survive and propagate in said host after step (b);

(d) detecting expression of said synthetic operon by detecting resolution of said cointegrate resulting in loss of said reporter gene.

13. The method of claim 1, wherein said artificial cointegrate is located in the chromosomal DNA of said microorganism.

14. The method of claim 1, wherein said artificial cointegrate within said microorganism is maintained on an autonomously replicating plasmid.

15. The method of claim 1, wherein said coding sequence is located in the chromosomal DNA of said microorganism.

16. The method of claim 1, wherein said coding sequence within said microorganism is maintained on an autonomously replicating plasmid.

* * * * *

UNITED STATES PATENT AND TRADEMARK OFFICE
CERTIFICATE OF CORRECTION

PATENT NO. : 5,512,452  
DATED : April 30, 1996  
INVENTOR(S) : John J. Mekalanos, Andrew Camilli Page 1 of 20

It is certified that error appears in the above-indentified patent and that said Letters Patent is hereby corrected as shown below:

In column 2, designated line 14, after the word "method" delete --.--.

In column 2, designated line 14, after the word "method" insert --see--.

In column 2, designated line 20, delete "chimefie" and substitute --chimeric--.

In column 2, designated line 43, delete "Xanthornonas" and substitute --Xanthomonas--.

In column 2, designated line 44, delete "promoterprobe" and substitute --promoter-probe--.

In column 2, designated line 50, delete "Xanthornonas" and substitute --Xanthomonas--.

In column 2, designated line 58, delete "rood" and substitute --mod--.

In column 2, designated line 58, delete "Antigenie" and substitute --Antigenic--.

In column 4, designated line 7, begin a new paragraph at the words "In the Drawings:".

In column 4, designated line 35, delete "chololerae" and substitute --cholerae--.

In column 4, designated line 45, delete "TnphoA" and substitute --TnphoA--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 4, designated line 46, delete "irgA" and substitute --*irgA*--.

In column 4, designated line 49, delete "irgA" and substitute --*irgA*--.

In column 5, designated line 56, delete "Tn,γδ" and substitute --Tnγδ--.

In column 5, designated line 62, delete "res" and substitute --*res*--.

In column 6, designated line 3, after "alternative" insert --,--.

In column 6, designated line 55, delete "calorimetric" and substitute --colorimetric--.

In column 6, designated line 61, delete "5'to" and substitute --5' to--.

In column 7, designated line 7, delete "Pi" and substitute --*Pi*--.

In column 7, designated line 13, delete "hi-parental" and substitute --bi-parental--.

In column 7, designated line 65, delete "calorimetric" and substitute --colorimetric--.

In column 8, designated line 43, after the word "monitored." begin a new paragraph.

In column 8, designated line 47, delete "TnphoA" and substitute --Tn*phoA*--.

In column 8, designated line 48, delete "TnphoA" and substitute --Tn*phoA*--.

In column 8, designated line 52, delete "TnphoA" and substitute --Tn*phoA*--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 8, designated line 56, delete "TnphoA" and substitute --TnphoA--.

In column 8, designated line 60, delete "TnphoA" and substitute --TnphoA--.

In column 8, designated line 61, delete "TnphoA" and substitute --TnphoA--.

In column 9, designated line 21, delete "eukaryofic" and substitute --eukaryotic--.

In column 9, designated line 22, delete "res" and substitute --res--.

In column 9, designated line 23, delete "res" and substitute --res--.

In column 9, designated line 54, delete "tnpR" and substitute --tnpR--.

In column 10, designated line 4, delete "res" and substitute --res--.

In column 10, designated line 7, delete "res" and substitute --res--.

In column 10, designated line 13, delete "tnpR" and substitute --tnpR--.

In column 10, designated line 15, delete "res1 tet res1" and substitute --res1 tet res1--.

In column 10, designated line 17, delete "tnpR" and substitute --tnpR--.

In column 10, designated line 18, delete "res1 tet res1" and substitute --res1 tet res1--.

In column 10, designated line 18, delete "res tet res" and substitute --res tet res--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 10, designated line 23, delete "res1" and substitute --*res1*--.

In column 10, designated line 27, delete "lacZ" and substitute --*lacZ*--.

In column 10, designated line 28, delete "lacZ::res1 tet res1" and substitute --*lacZ::res1 tet res1*--.

In column 10, designated line 28, delete "lacZ::res tet res" and substitute --*lacZ::res tet res*--.

In column 10, designated line 32, delete "unpublished)carrying" and substitute --unpublished) carrying--.

In column 10, designated lines 39/40, delete "res tet res" and substitute --*res tet res*--.

In column 10, designated line 44, delete "res tet res" and substitute --*res tet res*--.

In column 10, designated line 52, delete "Sin" and substitute --Sm--.

In column 10, designated line 59, delete "res1 tet res1" and substitute --*res1 tet res1*--.

In column 10, designated line 55, delete "pSKCAT2tnpR::res1 tet res1" and substitute --pSKCAT2*tnpR::res1 tet res1*--.

In column 11, designated line 2, delete "lacZ::res1 tet res1" and substitute --*lacZ::res1 tet res1*--.

In column 11, designated lines 2/3, delete "lacZ::res tet res" and substitute --*lacZ::res tet res*--.

In column 11, designated line 4, delete "tnpR" and substitute --*tnpR*--.

UNITED STATES PATENT AND TRADEMARK OFFICE
CERTIFICATE OF CORRECTION

PATENT NO. : 5,512,452

DATED : April 30, 1996

INVENTOR(S) : John J. Mekalanos, Andrew Camilli

It is certified that error appears in the above-indentified patent and that said Letters Patent is hereby corrected as shown below:

In column 11 designated lines 8, 12, 24 and 30, delete "lacZ" and substitute --*lacZ*--.

In column 11, designated line 7, delete "(res tet res" and substitute --(*res tet res*--.

In column 11, designated lines 7/8, delete "res1 tet res1)" and substitute --*res1 tet res1*)--.

In column 11, designated line 12, delete "res tet res" and substitute --*res tet res*--.

In column 11, designated line 25, delete "lacZ::pAC20" and substitute --*lacZ*::pAC20--.

In column 11, designated line 34, delete "Cm$^8$" and substitute --Cm$^S$--.

In column 11, designated line 34, delete "routants" and substitute --mutants--.

In column 11, designated line 36, delete "Latz" and substitute --LacZ--.

In column 11, designated line 36, delete "chromogenie" and substitute --chromogenic--.

In column 11, designated line 39, delete "lacZ::res tet res" and substitute --*lacZ*::*res tet res*--.

In column 11, designated line 50, delete "tnpR" and substitute --*tnpR*--.

In column 11, designated line 56, delete "TnphoA'" and substitute --Tn*phoA'*--.

In column 11, designated line 59, delete "TnphoA'" and substitute --Tn*phoA'*--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli Page 6 of 20

It is certified that error appears in the above-indentified patent and that said Letters Patent is hereby corrected as shown below:

In column 11, designated line 60, delete "tnpR" and substitute —tnpR—.

In column 11, designated line 62, delete "GrindIcy" and substitute —Grindley—.

In column 12, designated line 13, delete "Restfiction" and substitute —Restriction—.

In column 12, designated line 16, delete "carded" and substitute —carried—.

In column 12, designated line 23, delete "pSKCAT2tnpR" and substitute —pSKCAT2tnpR—.

In column 12, designated line 27, delete "trpA" and substitute —trpA—.

In column 12, designated line 35, delete "pSKCAT2tnpRT" and substitute —pSKCAT2tnpRT—.

In column 12, designated line 39, delete "Barn HI and Nru I." and substitute —Bam HI and Nru I.—.

In column 12, designated line 39, delete "lacZY" and substitute —lacZY—.

In column 12, designated line 39, delete "restfiction" and substitute —restriction—.

In column 12, designated line 40, delete "trp-lac" and substitute —trp-lac—.

In column 12, designated line 40, delete "lac" and substitute —lac—.

In column 12, designated line 42, delete "promotedess" and substitute —promoterless—.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 12, designated line 42, delete "lacZ$^+$, lacY$^+$" and substitute --lacZ$^+$, lacY$^+$--.

In column 12, designated line 45, delete "Kpn" and substitute --Kpn--.

In column 12, designated lines 46 & 47, delete "Kpn" and substitute --Kpn--.

In column 12, designated line 47, delete "pSKCAT2tnpRT" and substitute --pSKCAT2tnpRT--.

In column 12, designated line 47, delete "lacZY" and substitute --lacZY--.

In column 12, designated line 48, delete "lacZY" and substitute --lacZY--.

In column 12, designated line 51, delete "tnpR" and substitute --tnpR--.

In column 12, designated line 52, delete "lacZY" and substitute --lacZY--.

In column 12, designated line 54, delete "lacZY" and substitute --lacZY--.

In column 12, designated line 54, delete "tnpR" and substitute --tnpR--.

In column 12, designated line 55, delete "trpA" and substitute --trpA--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 12, designated line 58, delete "P/replication" and substitute --*Pi* replication--.

In column 13, designated line 12, delete "pIVETS" and substitute --pIVET5--.

In column 13, designated line 19, delete "pir" and substitute --*pir*--.

In column 13, designated line 21, delete "pir" and substitute --*pir*--.

In column 13, designated line 28, delete "pir" and substitute --*pir*--.

In column 13, designated line 20, delete "tnpR" and substitute --*tnpR*--.

In column 13, designated line 27, delete "carded" and substitute --carried--.

In column 13, designated line 55, delete "tnpR" and substitute --*tnpR*--.

In column 13, designated line 60, delete "lac" and substitute --*lac*--.

In column 13, designated line 61, delete "lac" and substitute --*lac*--.

In column 14, designated line 7, delete "tnpR" and substitute --*tnpR*--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 14, designated line 11, delete "tnpR lacZY" and substitute --*tnpR lacZY*--.

In column 14, designated line 22, delete "Latz" and substitute --*LacZ*--.

In column 14, designated line 24, delete "tnpR lacZY" and substitute --*tnpR lacZY*--.

In column 14, designated line 24, delete "Latz" and substitute --*LacZ*--.

In column 14, designated line 28, delete "tnpR lacZY" and substitute --*tnpR lacZY*--.

In column 14, designated line 29, delete "Latz" and substitute --*LacZ*--.

In column 14, designated line 33, delete "tnpR lacZY" and substitute --*tnpR lacZY*--.

In column 15, designated lines 3/4, delete "tnpR lacZY" and substitute --*tnpR lacZY*--.

In column 15, designated line 5, delete "res tet res" and substitute --*res tet res*--.

In column 15, designated line 5, delete "res1 tet res1" and substitute --*res1 tet res1*--.

In column 15, designated lines 17/18 delete "lacZ::res tet res" and substitute --*lacZ*::*res tet res*--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 15, designated line 18, delete "tnpR" and substitute --*tnpR*--.

In column 15, designated line 24, delete "tnpR lacZY" and substitute --*tnpR lacZY*--.

In column 15, designated line 40, delete DH5αλpir" and substitute --DH5αλ*pir*--.

In column 15, designated line 51, after "gene" insert --,--.

In column 15, designated line 59, delete "tnpR" and substitute --*tnpR*--.

In column 16, designated line 13, delete "lacZ::res tet res" and substitute --lacZ::*res tet res*--.

In column 16, designated lines 13/14, delete "lacZ::res1 tet res1" and substitute --lacZ::*res1 tet res1*--.

In column 16, designated line 15, delete "aileles" and substitute --alleles--.

In column 16, designated line 19, delete "tnpR lacZY" and substitute --*tnpR lacZY*--.

In column 16, designated line 27, delete "chromosoma" and substitute --chromosomal--.

In column 16, designated lines 27/28, delete "tnpR lacZY" and substitute --*tnpR lacZY*--.

UNITED STATES PATENT AND TRADEMARK OFFICE
CERTIFICATE OF CORRECTION

PATENT NO. : 5,512,452  
DATED : April 30, 1996  
INVENTOR(S) : John J. Mekalanos, Andrew Camilli Page 11 of 20

It is certified that error appears in the above-indentified patent and that said Letters Patent is hereby corrected as shown below:

In column 16, designated line 38, delete "containgres1 tet res1, "res1 tet res1"" and substitute --containing res1 tet res1, "res1 tet res1"--.

In column 16, designated line 39, delete "res1" and substitute --res1--.

In column 16, designated line 45, delete "pSKCAT2tnpR" and substitute --pSKCAT2tnpR--.

In column 16, designated line 45, delete "pSKCAT2tnpR::res1 tet res1" and substitute --pSKCAT2tnpR::res1 tet res1--.

In column 16, designated lines 46/47, delete "res1 tet res1" and substitute --res1 tet res1--.

In column 16, designated line 47, delete "pSKCAT2tnpR::res1 tet res1" and substitute --pSKCAT2tnpR::res1 tet res1--.

In column 16, designated line 51, delete "pSKCATtnpR" and substitute --pSKCATtnpR--.

In column 16, designated line 54, delete "res1" and substitute --res1--.

In column 16, designated lines 53 & 55, delete "res" and substitute --res--.

In column 16, designated line 62, delete "neogene" and substitute "neo gene--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 16, designated line 64, delete "Sac" and substitute --Sac--.

In column 16, designated line 65, delete "Sac" and substitute --Sac--.

In column 16, designated line 66, delete "Sac" and substitute --Sac--.

In column 16, designated line 66, delete "neo" and substitute --neo--.

In column 17, designated line 1, delete "TnphoA'" and substitute --TnphoA'--.

In column 17, designated line 4, delete "TnphoA" and substitute --TnphoA--.

In column 17, designated line 5, delete "TnphoA" and substitute --TnphoA--.

In column 17, designated line 7, delete "DH5α λpir" and substitute --DH5αλ pir--.

In column 17, designated line 8, delete "et aL" and substitute --et al.--.

In column 17, designated line 21, delete "Pit$^+$" and substitute --Pir$^+$--.

In column 17, designated line 31, delete "antigenie" and substitute --antigenic--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 17, designated line 35, delete "nieotinate" and substitute --nicotinate--.

In column 17, designated line 37, delete "B.pertussis" and substitute --B. pertussis--.

In column 17, designated line 43, delete "(vrg6::TnphoA)" and substitute --(vrg6::TnphoA)--.

In column 17, designated line 51, delete "vrg6::TnphoA" and substitute --vrg6::TnphoA--.

In column 17, designated line 53, delete "tnpR" and substitute --tnpR--.

In column 17, designated line 56, delete "IncP" and substitute --IncP--.

In column 17, designated line 58, delete "oriR6K" and substitute --oriR6K--.

In column 17, designated line 59, delete "Kolter," and substitute --(Kolter,--.

In column 17, designated line 60, delete "TnphoA" and substitute --TnphoA--.

In column 17, designated line 62, delete "TnphoA" and substitute --TnphoA--.

In column 17, designated line 62, delete "TnphoA'" and substitute --TnphoA'--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 17, designated line 63, delete "neo" and substitute --*neo*--.

In column 17, designated line 64, delete "SM10λpir" and substitute --SM10λ*pir*--.

In column 17, designated line 66, delete "Beeton" and substitute --Becton--.

In column 18, designated line 6, delete "TnphoA" and substitute --Tn*phoA*--.

In column 18, designated line 12, delete "TnphoA'" and substitute --Tn*phoA*'--.

In column 18, designated line 13, delete "TnphoA" and substitute --Tn*phoA*--.

In column 18, designated line 13, delete "B. pertussis" and substitute --*B. pertussis*--.

In column 18, designated line 18, delete "neo" and substitute --*neo*--.

In column 18, designated line 22, delete "routants" and substitute --mutants--.

In column 18, designated line 37, delete "tet" and substitute --*tet*--.

In column 18, designated line 63, delete "vrg6-tnpR" and substitute --*vrg6-tnpR*--.

UNITED STATES PATENT AND TRADEMARK OFFICE
CERTIFICATE OF CORRECTION

PATENT NO. : 5,512,452

DATED : April 30, 1996

INVENTOR(S) : John J. Mekalanos, Andrew Camilli

It is certified that error appears in the above-indentified patent and that said Letters Patent is hereby corrected as shown below:

In column 19, designated line 3, delete "AC-B 121" and substitute --AC-B121--.

In column 19, designated line 12, delete "(vrg6-TnphoA)" and substitute --(vrg6::TnphoA)--.

In column 19, designated line 17, delete "dam" and substitute --data--.

In column 19, designated line 20, delete "maerophages" and substitute --macrophages--.

In column 19, designated line 25, delete "vrg6-tnpR" and substitute --vrg6-tnpR--.

In column 19, designated line 25, delete "AC-B12 1" and substitute --AC-B121--.

In column 20, designated line 6, delete "dam" and substitute --data--.

In column 20, designated line 7, delete "intracelhlar" and substitute --intracellular--.

In column 20, designated line 11, delete "aleionized" and substitute --deionized--.

In column 20, designated line 14, delete "Sm 101" and substitute --Sm, 100--.

In column 20, designated line 18, delete "vrg6-tnpR" and substitute --vrg6-tnpR--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 20, designated line 34, delete "vrg6-tnpR" and substitute --vrg6-tnpR--.

In column 20, designated lines 42/43, delete "Vibrio cholerae irgA::TnphoA" and substitute --Vibrio cholerae irgA::TnphoA--

In column 20, designated line 44, delete "irgA::tnpR" and substitute --irgA::tnpR--.

In column 20, designated line 44, delete "AHelic" and substitute --Allelic--.

In column 20, designated line 52, delete "(irgA::TnphoA)" and substitute --(irgA::TnphoA)--.

In column 20, designated line 59, delete "irgA::TnphoA" and substitute --irgA::TnphoA--.

In column 20, designated line 60, delete "tnpR" and substitute --tnpR--.

In column 20, designated line 63, delete "TnphoA" and substitute --TnphoA--.

In column 20, designated line 66, delete "TnphoA" and substitute --TnphoA--.

In column 20, designated line 66, delete "TnphoA'" and substitute --TnphoA'--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 20, designated line 66, delete "neo" and substitute --*neo*--.

In column 21, designated line 4, delete "DH5αλpir" and substitute --DH5αλ*pir*--.

In column 21, designated line 7, delete "DH5αλpir" and substitute --DH5αλ*pir*--.

In column 21, designated line 10, delete "TnphoA" and substitute --Tn*phoA*--.

In column 21, designated line 13, delete "TnphoA'" and substitute --Tn*phoA'*--

In column 21, designated line 14, delete "TnphoA" and substitute --Tn*phoA*--.

In column 21, designated line 21, delete "neo" and substitute --*neo*--.

In column 21, designated line 23, delete "KM$^r$" and substitute --Km$^r$--.

In column 21, designated line 25, delete "30/μg/ml" and substitute "30 μg/ml--.

In column 21, designated line 43, delete "tet" and substitute --*tet*--.

In column 22, designated line 20, delete "irgA" and substitute --*irgA*--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 22, designated line 21, delete "$[Fe^{2+}]$" and substitute --$[Fe^{2+}]$--.

In column 22, designated line 22, delete "-dipyfidyl" and substitute ---dipyridyl--.

In column 22, designated line 28, delete "res1 tet res1" and substitute --res1 tet res1"

In column 22, designated line 33, delete "tet" and substitute --tet--.

In column 22, designated line 36, delete "tet" and substitute --tet--.

In column 22, designated line 39, delete "tnpR" and substitute --tnpR--.

In column 22, designated line 40, delete "phoA" and substitute --phoA--.

In column 22, designated line 43, delete "res1 tet res1" and substitute --res1 tet res1--.

In column 22, designated line 62, delete "irgA-tnpR" and substitute --irgA-tnpR--.

In column 23, designated line 4, delete "replicaplat-ing" and substitute --replica-plating--.

In column 23, designated line 9, delete "irgA-tnpR" and substitute --irgA-tnpR--.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 23, designated line 27, delete "irgA-tnpR" and substitute —*irgA-tnpR*—.

In column 23, designated line 31, delete "irgA-tnpR" and substitute —*irgA-tnpR*—.

In column 23, designated line 33, delete "irgA-inducing" and substitute —*irgA-inducing*—.

In column 23, designated line 43, delete "irgA-tnpR" and substitute —*irgA-tnpR*—.

In column 23, designated line 46, delete (j.p.) and substitute —(i.p.)—.

In column 24, designated line 9, delete "irgA-tnpR" and substitute —*irgA-tnpR*—.

In column 27, designated line 55, delete "choosing" and substitute —(j) choosing—.

In column 27, designated line 60, delete "of host" and substitute —of a host—.

In column 28, designated line 53, after the word "plasmids" insert —;—.

UNITED STATES PATENT AND TRADEMARK OFFICE
CERTIFICATE OF CORRECTION

PATENT NO. : 5,512,452
DATED : April 30, 1996
INVENTOR(S) : John J. Mekalanos, Andrew Camilli It is certified that error appears in the above-indentified patent and that said Letters Patent is hereby corrected as shown below:

In column 12, designated line 10, 30 and 33, delete "tnpR" and substitute --tnpR--.
In column 12, designated 31, delete "pSKCAT2tnpR" and substitute --pSKCAT2tnpR--.
In column 12, designated line 46, delete "Kpn" and substitute --Kpn--.
In column 12, designated line 51, delete "lacZY" and substitute --lacZY--.

In column 15, designated lines 51 and 53, delete "tnpR" and substitute --tnpR--.

In column 16, designated line 39, delete "tet" and substitute --tet--.

Signed and Sealed this

Twenty-second Day of April, 1997

Attest:

BRUCE LEHMAN

*Attesting Officer*

*Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:

(A) LENGTH: 46 base pairs
        (B) TYPE: nucleic acid
        (C) STRANDEDNESS: single
        (D) TOPOLOGY: linear (iii) HYPOTHETICAL: YES (iv) ANTI-SENSE: NO (vi) ORIGINAL SOURCE:
        (A) ORGANISM: DNA (other)

(xi) SEQUENCE DESCRIPTION: SEQ ID NO:1:

ATGATGTCGA CTCTAGAGAT CTGATTTAGG ATACATTTTT ATGCGA        46

(2) INFORMATION FOR SEQ ID NO:2:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO:2:

ATGATGTCGA CGAGCTCGGT ACCTTTTATG TTAGTTGCTT TCATTT        46

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: DNA (other)

(xi) SEQUENCE DESCRIPTION: SEQ ID NO:3:

AGCCCGCCTA ATGAGCGGGC TTTTTTTT        28